(12) United States Patent
Leisk et al.

(10) Patent No.: US 11,701,450 B2
(45) Date of Patent: *Jul. 18, 2023

(54) INJECTABLE SILK FIBROIN FOAMS AND USES THEREOF

(71) Applicant: Trustees of Tufts College, Medford, MA (US)

(72) Inventors: Gary G. Leisk, Somerville, MA (US); Tim Jia-Ching Lo, Taoyuan (TW); Lei Li, Beijing (CN); Evangelia Bellas, Philadelphia, PA (US); David L. Kaplan, Concord, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 15/273,327

(22) Filed: Sep. 22, 2016

(65) Prior Publication Data
US 2017/0007738 A1  Jan. 12, 2017

Related U.S. Application Data

(63) Continuation of application No. 14/357,420, filed as application No. PCT/US2012/064471 on Nov. 9, 2012, now Pat. No. 9,492,504.

(60) Provisional application No. 61/557,610, filed on Nov. 9, 2011.

(51) Int. Cl.
| | |
|---|---|
| A61L 27/56 | (2006.01) |
| A61L 27/50 | (2006.01) |
| A61L 27/22 | (2006.01) |
| A61L 27/36 | (2006.01) |
| A61L 27/38 | (2006.01) |
| A61L 27/48 | (2006.01) |
| A61L 27/54 | (2006.01) |
| A61K 38/17 | (2006.01) |
| A61L 27/58 | (2006.01) |

(52) U.S. Cl.
CPC ........ A61L 27/227 (2013.01); A61K 38/1767 (2013.01); A61L 27/3604 (2013.01); A61L 27/3834 (2013.01); A61L 27/48 (2013.01); A61L 27/50 (2013.01); A61L 27/54 (2013.01); A61L 27/56 (2013.01); A61L 27/58 (2013.01); A61L 2400/06 (2013.01); A61L 2400/08 (2013.01); A61L 2430/34 (2013.01)

(58) Field of Classification Search
CPC .. A61L 2430/34; A61L 27/48; A61L 2400/06; A61L 27/56; A61L 27/50; A61L 27/255; A61L 31/046; A61L 29/146; A61K 2800/91; A61K 9/0019; A61K 31/728
See application file for complete search history.

(56) References Cited

U.S. PATENT DOCUMENTS

| | | | |
|---|---|---|---|
| 6,673,285 B2 | 1/2004 | Ma | |
| 7,662,409 B2 | 2/2010 | Masters | |
| 9,492,504 B2 | 11/2016 | Leisk et al. | |
| 2008/0075749 A1* | 3/2008 | Dyer | A61K 9/0019 424/422 |
| 2008/0085272 A1* | 4/2008 | Kaplan | A61K 9/7007 424/130.1 |
| 2008/0107744 A1* | 5/2008 | Chu | A61F 2/0036 424/489 |
| 2008/0213564 A1 | 9/2008 | Ma et al. | |
| 2008/0317816 A1 | 12/2008 | Ma et al. | |
| 2009/0028817 A1* | 1/2009 | Niklason | A61K 8/64 424/85.2 |
| 2009/0214649 A1 | 8/2009 | Gazit et al. | |
| 2010/0016907 A1* | 1/2010 | Vresilovic | A61F 2/442 606/86 R |
| 2010/0279112 A1* | 11/2010 | Kaplan | A61L 27/227 428/357 |
| 2010/0317587 A1* | 12/2010 | Chung | A61L 27/227 514/16.7 |
| 2011/0020409 A1 | 1/2011 | Altman et al. | |
| 2011/0189292 A1 | 8/2011 | Lebreton et al. | |
| 2011/0223153 A1* | 9/2011 | Lu | A61L 27/3604 424/130.1 |
| 2013/0109836 A1* | 5/2013 | Kobayashi | A61K 8/64 530/353 |
| 2014/0314817 A1 | 10/2014 | Leisk et al. | |

FOREIGN PATENT DOCUMENTS

| | | |
|---|---|---|
| WO | WO-01/87267 A1 | 11/2001 |
| WO | WO-2005/020849 A2 | 3/2005 |
| WO | WO-2010/123945 A2 | 10/2010 |
| WO | WO-2010/123947 A2 | 10/2010 |

OTHER PUBLICATIONS

Extended European Search Report for EP 12846855.0, 6 pages (dated Apr. 24, 2015).
International Search Report for PCT/US2012/064471, 6 pages (dated Apr. 1, 2013).
Written Opinion for PCT/US2012/064471, 5 pages (dated Apr. 1, 2013).

* cited by examiner

*Primary Examiner* — Tracy Liu
(74) *Attorney, Agent, or Firm* — GTC Law Group PC & Affiliates

(57) ABSTRACT

The inventions provided herein relate to compositions, methods, delivery devices and kits for repairing or augmenting a tissue in a subject. The compositions described herein can be injectable such that they can be placed in a tissue to be treated with a minimally-invasive procedure (e.g., by injection). In some embodiments, the composition described herein comprises a compressed silk fibroin matrix, which can expand upon injection into the tissue and retain its original expanded volume within the tissue for a period of time. The compositions can be used as a filler to replace a tissue void, e.g., for tissue repair and/or augmentation, or as a scaffold to support tissue regeneration and/or reconstruction. In some embodiments, the compositions described herein can be used for soft tissue repair or augmentation.

25 Claims, 11 Drawing Sheets

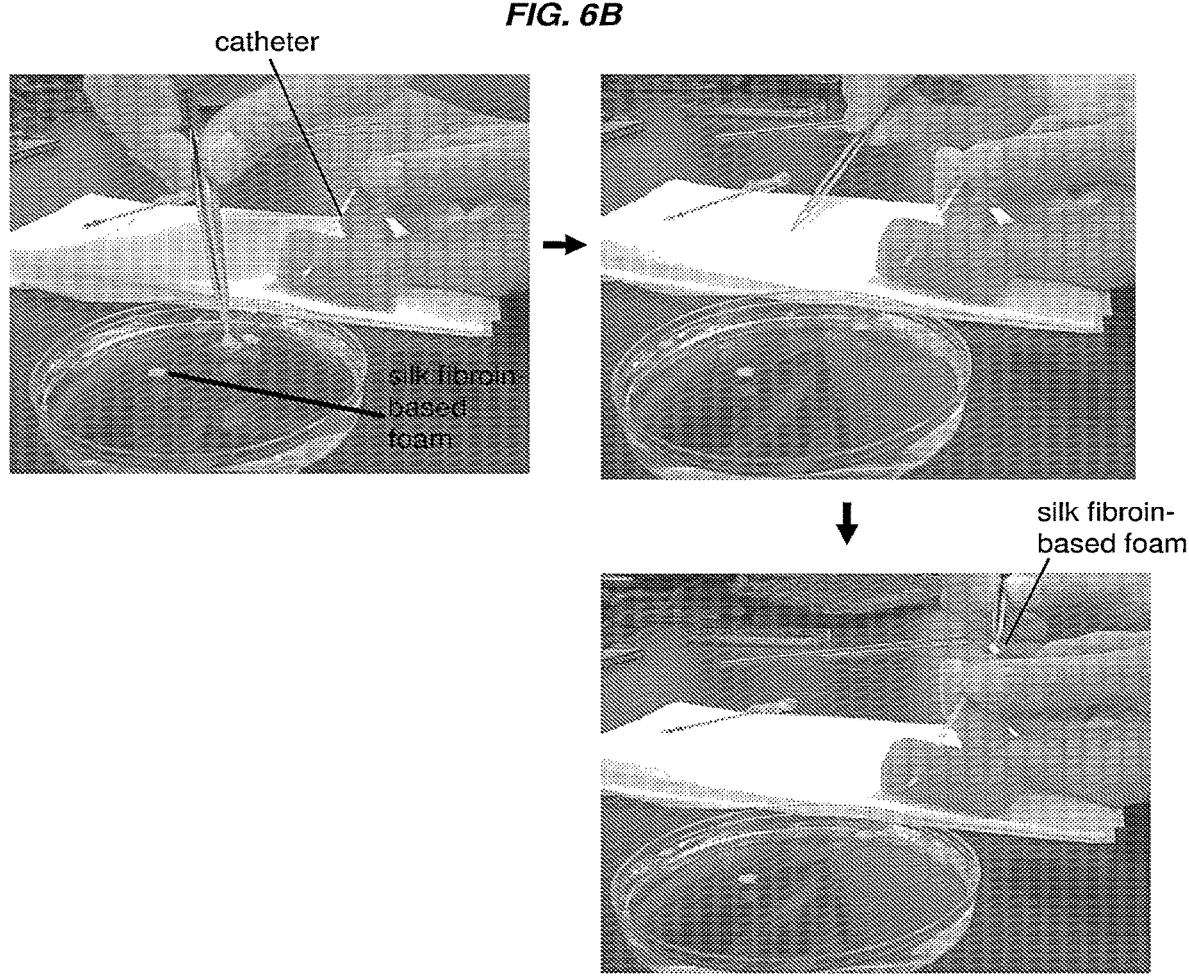

INJECTABLE SILK FIBROIN FOAMS AND USES THEREOF

CROSS REFERENCE TO RELATED APPLICATIONS

The present application claims the benefit of U.S. patent application Ser. No. 14/357,420, filed on May 9, 2014, which application is a National Stage Entry of PCT/US2012/064471, filed on Nov. 9, 2012, which further claims priority to U.S. provisional patent application Ser. No. 61/557,610, filed Nov. 9, 2011, the entire disclosure of each of which is incorporated herein by reference.

GOVERNMENT SUPPORT

This invention was made with government support under Grant No. EB002520 awarded by the National Institutes of Health and W81XWH-08-2-0032 awarded by the US Army. The government has certain rights in the invention.

TECHNICAL FIELD OF THE DISCLOSURE

The inventions described herein generally relate to silk fibroin-based materials for biomedical applications, e.g., in soft tissue repair, augmentation and/or reconstruction.

BACKGROUND

The restoration of soft tissue defects from trauma, surgical excision or congenital defects should start with a strategy that will maintain tissue size and shape to near normal dimensions for extended time frames. Current clinical strategies include free fat transfers and artificial fillers. In the case of breast cancer patients receiving mastectomies, silicone shells filled with saline or silicone are used to replace the void. This leaves the patient with an unnatural look and feel, and the risk of capsular contracture resulting in a revision surgery. The fat grafting and artificial filler options fail to retain volume over time. Thus, the fat grafting and artificial filler options can require a second surgical site, have avascular necrosis and generally do not regenerate the original tissue.

Bovine and human collagen have gained widespread use as injectable materials for soft tissue augmentation and filling. Collagen, the principal extracellular structural protein of the animal body, has been used as an implant material to replace or augment connective tissue, such as skin, tendon, cartilage and bone. Additionally, collagen has been injected or implanted into the human body for cosmetic purposes for a number of years. However, the use of collagen in soft tissue augmentation and/or filling could be costly and it does not have a long lasting effect, e.g., the results often only last for about 3 months.

Hyaluronic acid (HA) is a glycosaminoglycan that is naturally found in the human body and is widely distributed throughout connective, epithelial, and neural tissues. Compositions of non-crosslinked hyaluronic acid tend to degrade within a few months after injection and thus require fairly frequent reinjection to maintain their soft tissue augmenting effect. More recently, compositions of cross-linked hyaluronic acid have been used for soft tissue augmentation. However, such cross-linked compositions contain fairly large particles, around approximately 2 mm each, of hyaluronic acid suspended in a gel. While the larger particles could have a longer lasting effect, the larger particle size can make the injection more challenging and create an unpleasant experience to a recipient.

In summary, the major disadvantages of the current strategies for soft tissue regeneration, repair and/or augmentation include a large amount of tissues required for grafting large tissue defects; donor site morbidity, possibility of second surgical site, avascular necrosis; loss of shape and/or size of the scaffolds over time; material mismatch with native tissue; and failure to regenerate tissue. Accordingly, there is a strong need to develop a strategy or a scaffold that can be administered with a minimally invasive procedure and will provide sustained retention of volume restoration for at least 3 months or longer, e.g., for at least 6 months or at least one year, while the body gradually remodels and regenerates the site into near-normal tissue structure and function.

SUMMARY

Spongy biomaterial scaffolds such as foams are desirable in tissue engineering, e.g., for soft tissue regeneration, repair and/or augmentation, partly because the network of interconnected pores within the spongy scaffolds is advantageous for cell attachment, yet allowing nutrient and waste flows. However, the mechanical property and/or structure of the current biomaterial foams generally fail to regenerate tissue or retain their volume within the tissue for an extended period of time. In addition, placement of such spongy biomaterial scaffolds in the tissue can be invasive. Therefore, it is imperative to develop a minimally-invasive strategy for repairing or augmenting a tissue in an individual, e.g., developing an injectable foam where the injectable foam can retain their volume and shape while the tissue gradually regenerates to restore its structure and function.

Embodiments of various aspects described herein are based on, at least in part, our discovery that the silk fibroin-based foam can be injected to fill void space in soft tissue, for example, soft tissue lost due to injury or disease—such as in trauma, cancer resection surgeries, breast reconstruction, breast augmentation, and related needs. In addition, the silk fibroin-based foam constructs can also be used for cosmetic purposes, for example, as a more cost-effective and natural alternative to topical treatments or BOTOX® treatments.

Accordingly, one aspect provided herein is an injectable composition for use in repairing or augmenting a tissue in a subject, comprising a compressed silk fibroin matrix, wherein the compressed silk fibroin matrix expands upon injection into the tissue, and retains at least a portion (e.g., at least about 1%, at least about 5%, at least about 10%, at least about 25%, at least about 50% or more) of its original expanded volume within the tissue to be repaired or augmented for a period of time (e.g., at least about 2 weeks, at least about 3 weeks, at least about 4 weeks, at least about 5 weeks, at least about 6 weeks or longer).

Another aspect provided herein relates to a method for repairing or augmenting a tissue in a subject. The method includes placing in the tissue to be repaired or augmented a composition comprising a compressed silk fibroin matrix, wherein the compressed silk fibroin matrix expands upon placement into the tissue, and retains at least a portion of its original expanded volume (e.g., at least about 1%, at least about 5%, at least about 10%, at least about 25%, at least about 50% or more) within the tissue for a period of time (e.g., at least about 2 weeks, at least about 3 weeks, at least about 4 weeks, at least about 5 weeks, at least about 6 weeks or longer). In one embodiment, the composition is placed into the tissue to be repaired or augmented by injection.

In some embodiments, the silk fibroin matrix can be provided in a compressed state for the treatment methods described herein. In some embodiments, the silk fibroin matrix can be provided in an uncompressed state, and can then be compressed to a smaller volume during loading into a delivery applicator an injection applicator such as a needle, cannula, and/or a catheter) before placing into a tissue to be repaired or augmented.

In some embodiments of the compositions and methods provided herein, the compressed silk fibroin matrix after placed (e.g., injected) into the tissue can expand in volume by at least about 50%, at least about 100%, at least about 2-fold, at least about 3-fold or more, as compared to the compressed volume of the silk fibroin matrix.

In certain embodiments of the compositions and methods provided herein, the silk fibroin matrix can exclude an amphiphilic peptide. In other embodiments, the silk fibroin matrices can include an amphiphilic peptide. An exemplary amphiphilic peptide, for example, can comprise a RGD motif.

In some embodiments of the compositions and methods provided herein, the silk fibroin matrix can retain at least about 50% of its expanded original volume, including at least about 60%, at least about 70%, at least about 80% or more, of its original expanded volume within the tissue for a period of time.

In some embodiments of the composition and method provided herein, the silk fibroin matrix can retain at least a portion of its original expanded volume for at least about 6 weeks, at least about 3 months, at least about 6 months or longer.

Volume retention of the silk fibroin matrix can be, in part, controlled by modulating the degradation and/or solubility properties of the silk fibroin matrix. For example, the silk fibroin matrix can be adapted to degrade at a pre-determined rate such that the silk fibroin matrix can maintain a desirable volume over a pre-determined period of time, e.g., to promote tissue regeneration or repair. For example, in such embodiments, the silk fibroin matrix can be adapted to degrade no more than 50% of its original expanded volume, for example, including no more than 30%, no more than 10%, of its original expanded volume, in at least about 2 weeks, including at least about 6 weeks, at least about 3 months, at least about 6 months or longer.

In some embodiments, the silk fibroin matrix can be adapted to degrade at a pre-determined rate such that the volume of the silk fibroin matrix gradually decreases (while still providing sufficient support) as a tissue placed with the silk fibroin matrix begins to regenerate. In such embodiments, the silk fibroin matrix can be adapted to degrade at least about 5% of its original expanded volume, for example, including at least about 10%, at least about 20%, at least about 30% or more, of its original expanded volume, in at least about 2 weeks, including at least about 6 weeks, at least about 3 months, at least about 6 months or longer.

Depending on the defect size of the tissue and/or desired properties of the silk fibroin matrix, the silk fibroin matrix (prior to compression) can be adapted to be any size. In some embodiments, the silk fibroin matrix (prior to compression) can have a size of about 1 mm to about 5 mm in diameter. In some embodiments, the silk fibroin matrix (prior to compression) can have a size larger than 5 mm in diameter. Since the silk fibroin matrix is compressible, the size of the silk fibroin matrix can be as large as feasible to fill larger sized defects provided that the size of the compressed silk fibroin matrix is feasible for injection into a tissue.

The silk fibroin matrix can be adapted to mimic the structural morphology of native tissues and/or to deliver an active agent to a local area of a tissue. For example, the silk fibroin matrix can be porous. In some embodiments, the porosity of the silk fibroin matrix can be adapted to mimic the structural morphology and/or gradient of cellular densities found in native tissue. In some embodiments, the porosity of the silk fibroin matrix can be adapted to deliver an active agent to a tissue in a pre-determined release profile. In some embodiments, the porosity of the silk fibroin matrix can be adapted to retain at least a portion of its original expanded volume for a period of time. For example, the silk fibroin porous matrix can have a porosity of at least about 1%, including, e.g., at least about 3%, at least about 5%, at least about 10%, at least about 15%, at least about 20%, at least about 25%, at least about 30%, at least about 40%, at least about 50%, at least about 70%, at least about 80%, at least about 90% or higher. The pore size of such porous silk fibroin matrix can range from about 1 μm to about 1500 μm, from about 50 μm to about 650 μm, or from about 100 μm to about 600 μm.

The silk fibroin matrix, in one embodiment, can be fabricated by freeze-processing a silk fibroin solution. In some embodiments, the silk fibroin solution can have a concentration of about 0.5% w/v to about 10% w/v, or about 1% w/v to about 6% w/v.

In some embodiments of any aspects described herein, the silk fibroin matrix can be a silk fibroin foam.

In some embodiments, the silk fibroin matrix or the compositions described herein can further comprise a hydrogel material.

The injectable composition described herein comprising the silk fibroin matrix can further comprise at least one active agent. In some embodiments, the silk fibroin matrix of the composition described herein can further comprise at least one active agent. Non-limiting examples of the active agents can include biologically active agents, cosmetically active agents, cell attachment agents, a dermal filler material, and any combinations thereof. In some embodiments, the active agent can be a cell, e.g., without limitations, a stem cell. In some embodiments, the active agent can be an adipose-derived stem cell. In some embodiments, the active agent can be a biological fluid or concentration, e.g., without limitations, a lipoaspirate or a bone marrow aspirate. In some embodiments, the active agent can be a therapeutic agent. In some embodiments, the active agent can be a cosmetically active agent. In some embodiments, the active agent can be a dermal filler material.

Various embodiments of the composition described herein can be injected into a tissue to be repaired or augmented by any known methods in the art, e.g., subcutaneously, submuscularly, or intramuscularly. When injected in a tissue, some embodiments of the composition can be at least partially dry. Alternatively, the composition can be at least partially hydrated. In some embodiments, the composition can further comprise a carrier, e.g., a buffered solution and/or a biological fluid or concentrate (e.g., a lipoaspirate), when injected in a tissue.

The tissue to be repaired or augmented by the composition and/or the method described herein can be a soft tissue. Exemplary examples of a soft tissue include, but are not limited to, a tendon, a ligament, skin, a breast tissue, a fibrous tissue, a connective tissue, a muscle, and any combinations thereof. In certain embodiments, the soft tissue is skin. In other embodiments, the soft tissue is a breast tissue.

A delivery device comprising one embodiment of an injectable composition and/or silk fibroin matrix is also provided herein. A delivery device can include an injection device (e.g., in a form of a syringe or an injection gun) and/or any administration device that is minimally invasive. Accordingly, in some embodiments, provided herein relate to an injection device comprising an injectable composition described herein. The delivery or injection device can further comprise a tubular structure for introducing the fibroin matrix or the composition described herein into a tissue to be repaired or augmented. The tubular structure can be tapered (e.g., comprising a conical interior space), e.g., to facilitate loading of the compressed fibroin matrix therein. In some embodiments, the tubular structure can permit compression of a silk fibroin matrix to a pre-determined volume (e.g., interior volume of the tubular structure) while loading the silk fibroin matrix therein. Examples of the tubular structure include, but are not limited to, a needle, a cannula, a catheter, or any combinations thereof. In some embodiments, the tubular structure can be pre-loaded with the silk fibroin matrix. In this embodiment, the silk fibroin matrix can be in a compression state inside the tubular structure. In some embodiments, the delivery or injection device can further comprise a mechanical element (e.g., an elongated rod-like structure) to facilitate the exit of the compressed silk fibroin matrix through the tubular structure. In some embodiments, the delivery or injection device can further comprise an injection carrier. In some embodiments, the delivery or injection device can further comprise a local anesthetic.

In some embodiments of any aspects described herein, the compositions and/or delivery devices can be stored or transported at a temperature about 0° C. and about 60° C., e.g., between about 1.0° C. and about 60° C. or between about 15° C. and about 60° C. At such temperatures, the bioactivity of active agents embedded or distributed inside the silk fibroin matrix can be stabilized for a period of time.

BRIEF DESCRIPTION OF THE DRAWINGS

FIG. 1A shows an image of a silk fibroin-based injectable foam disk being excised, e.g., using a 4 mm biopsy punch. FIG. 1B shows an image of a silk fibroin-based injectable foam disk after excision.

FIG. 2A shows an image of a silk fibroin-based injectable foam disk being loaded into a pipette tip. FIG. 2B shows an image of a silk fibroin-based injectable foam disk being tamped into an injection position inside a pipette tip, e.g., using a stiff wire.

FIG. 3A shows an image of puncturing a hole in the tissue of the chicken thigh, e.g., using a straight 14-gauge needle. FIG. 3B shows an image of inserting into a hole a pipette tip containing a silk fibroin-based injectable foam disk (e.g., as shown in FIG. 2B). FIG. 3C shows an image of ejecting the silk fibroin-based foam disk, e.g., using a stiff wire, into the tissue while slowly drawing out the pipette tip. FIG. 3D shows an image of the injectable silk fibroin-based foam disk positioned in the raw chicken thigh (black arrow denotes the silk fibroin-based foam disk injected into the tissue).

FIG. 4A shows an image of palpation of a tissue (e.g., raw chicken tissue) for the injected silk fibroin-based foam. FIG. 4B shows an image of an incision (e.g., made with a razor blade) dose to where the embedded silk fibroin-based foam is located. FIG. 4C shows an image of exposure of the embedded silk fibroin-based foam after the incision. FIG. 4D shows another perspective view of the silk fibroin-based foam from FIG. 4C in cross-section. FIG. 4E shows an image of removing the exposed silk fibroin-based foam (e.g., using a pair of tweezers). FIG. 4F shows an image of the silk fibroin-based foam extracted from the tissue.

FIGS. 6A-6C show images of another exemplary method of injecting a silk fibroin-based injectable foam disk into a tissue-like material. FIG. 6A is a series of images showing steps of preparing a catheter for injecting a silk fibroin-based foam into a tissue. A hole is punctured in a target area of the tissue, so that a catheter can be inserted into the hole. FIG. 6B is a series of images showing steps of loading a silk fibroin-based foam into the catheter inserted into the tissue. After inserting the catheter into a tissue, a silk fibroin-based foam is loaded into the catheter, e.g., via an adaptor. FIG. 6C is a series of images showing steps of pushing as silk fibroin-based foam through a catheter. After loading the silk fibroin-based foam into the adaptor to the catheter, a rod is used to push the foam down through the catheter into the tissue.

FIG. 7A is an exemplary custom-modified injection gun for use to facilitate the injection of a silk fibroin-based foam into a tissue in vivo. A foam ramrod is being placed into the injection gun. FIG. 7B is a series of images showing exemplary steps of injecting a silk fibroin-based foam into a tissue in a rat or mouse model. A catheter (e.g., with a gauge of 14G) is inserted into a target tissue area, followed by a silk fibroin-based foam loaded into the catheter. The catheter is then connected to a foam injector (e.g., the injection gun as shown in FIG. 7A), so that the silk fibroin-based foam can be injected slowly through the catheter into the target tissue area (e.g., subcutaneous area).

FIGS. 8A-8C show images of silk fibroin-based foams injected into a rat model in vivo after the removal of the rat skin. Silk fibroin-based foams produced from different concentrations of silk fibroin solution (e.g., 1%, 3%, 6% silk fibroin) and sources of cocoon (Japanese: JP vs. Taiwanese: TW) were evaluated after injection for 1 day (FIG. 8A), 14 days (FIG. 8B) and 30 days (FIG. 8C). FIG. 8A shows that the injected silk fibroin-based foams remained clear 1 day after injection, unless they were stained by blood due to a puncture into a blood vessel (e.g., TW3). FIGS. 8B-8C show that the injected silk fibroin-based foams obtained a reddish hue about 14 days and about 30 days, respectively, after injection. However, there appeared no significant change in vascularization leading to the injected foams. FIG. 8D shows an image of the injected foams visible from outside skin of a rat. FIG. 8E is a set of images showing gross morphology of some embodiments of the silk fibroin-based injectable foams (corresponding to the ones in FIGS. 8A-8C) explanted after an indicated post-injection period (e.g., 1 day, 14 days and 30 days post-injection). There are no observable visual differences in gross morphology at the indicated timepoints. The silk fibroin foams are consistently stiffer with increased silk weight percentage. All explants are soft to the touch and return to their original shape after deformation. FIG. 8F shows the volume retention results of the fibrin-based foams after injection into the tissue for 1 day or 14 days. FIG. 8G shows the volume retention results of the silk fibroin-based foams after injection into the tissue for 14 days, 30 days or 60 days. The results of FIGS. 8F and 8G are expressed in percents of volume retained relative to the original volume.

DETAILED DESCRIPTION OF THE INVENTION

Figure 1A:
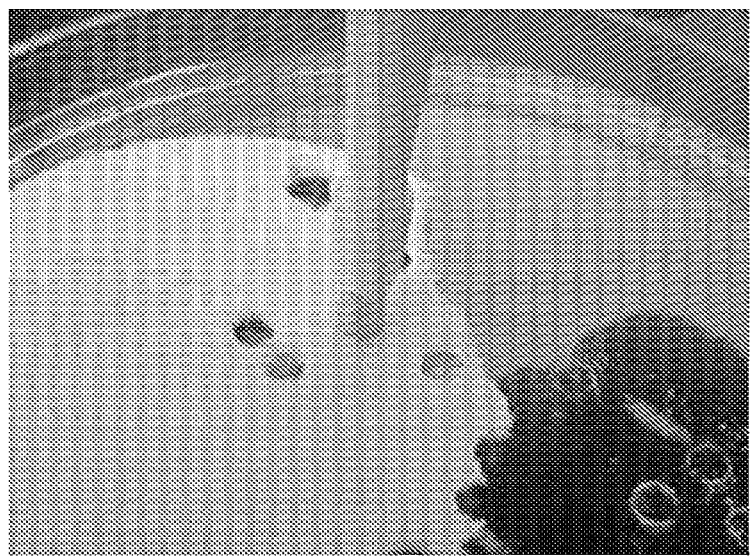
FIGS. 1A-1B show images of silk fibroin-based injectable foam disks in accordance with one or more embodiments described herein.

Described herein are methods, compositions, delivery devices, and kits for repairing or augmenting a tissue in a subject. In accordance with embodiments of various aspects described herein, a reversibly-deformable and/or injectable format of silk fibroin scaffolds (e.g., sills fibroin foams) can be compressed (e.g., to a smaller volume) and placed (e.g., by injection) into a tissue to be repaired or augmented. Upon placement (e.g., injection) into the tissue, the compressed silk fibroin matrix expands to a volume (e.g., an increase in volume by at least about 10% of its compressed volume) and retains at least a portion of its original expanded volume (e.g., at least about 50% of its original expanded volume or more) within the tissue to be repaired or augmented for a period of time (e.g., at least about 2 weeks or longer). Such reversibly-deformable and/or injectable silk fibroin matrix can be introduced into a defect site with a minimally-invasive procedure.

Silk Fibroin Matrix

Silk fibroin matrices described herein are deformable. The silk fibroin matrices can be compressed prior to and/o during placement (e.g., injection) into a tissue to be repaired or augmented. Upon placement (e.g., injection) into the tissue, the compressed silk fibroin matrices can then expand within the tissue and retain its original expanded volume within the tissue for a period of time.

As used herein, the term "deformable" generally refers to the ability of an object to change size (e.g., volume) and/or shape in response to an external pressure/force, while maintaining the integrity of the object (i.e., the object remains intact as a whole, without breaking into pieces, during deformation, and has the ability to restore at least a portion of its original size and shape). With respect to a deformable silk fibroin matrix, the silk fibroin matrix can decrease its volume and/or change its shape when compressed by an applied force such that the silk fibroin matrix becomes small enough (but intact) to be loaded into an injection applicator (e.g., a needle, a cannula, or a catheter) having a dimension much smaller than that of the uncompressed silk fibroin matrix, and/or that the silk fibroin matrix are compressed to adopt the cross-sectional shape of the injection applicator.

As used herein, the term "compressed" generally refers to a decrease in volume of a silk fibroin matrix. In some embodiments, a decrease in volume of a silk fibroin matrix can also lead to a change in one or more physical properties of the silk fibroin matrix, e.g., an increase in original density (before compression) of the silk fibroin matrix, a decrease in original pore size (before compression) and/or original porosity (before compression) of the silk fibroin matrix. Compression of a silk fibroin matrix to a pre-determined volume can be performed by any known methods in the art, e.g., by physical loading of a silk fibroin matrix into the interior space of a delivery applicator (e.g., a needle, cannula or a catheter), or by vacuum.

In some embodiments, the silk fibroin matrix can be compressed to a volume of no more than 80% of its original volume (i.e. the volume of the silk fibroin matrix before compression), including no more than 70%, no more than 60%, no more than 50%, no more than 40%, no more than 30%, no more than 20%, no more than 10%, no more than 5% or lower, of its original volume (i.e., the volume of the silk fibroin matrix before compression). In some embodiments, the silk fibroin matrix can be compressed to a volume of at least about 10% of its original volume (i.e., the volume of the silk fibroin matrix before compression), including at least about 20%, at least about 30%, at least about 40%, at least about 50%, at least about 60%, at least about 70%, at least about 80%, at least about 90% or more, but excluding 100%, of its original volume (i.e., the volume of the silk fibroin matrix before compression). In some embodiments, silk fibroin matrix, such as silk fibroin foams, fabricated from a silk fibroin solution with concentrations of about 1% to about 6% can be compressed to approximately 20% to 30% of their original volume. The amount of compression possible without breaking or causing permanent deformation of the silk fibroin matrix is dependent on, for example, the material properties, silk fibroin concentration, and/or fabrication/process methods and parameters. In some embodiments, higher molecular weight of the matrix or other improved processing can yield higher levels of compression of a silk fibroin-based matrix, e.g., a silk fibroin-based matrix compressed to less than 20% of its original volume.

In some embodiments, the silk fibroin matrix can be compressed to a volume that increase the original density (e.g., ratio of weight to uncompressed volume) of the silk fibroin matrix by at least about 10%, including, e.g., at least about 20%, at least about 30%, at least about 40%, at least about 50%, at least about 60%, at least about 70%, at least about 80%, at least about 90%, at least about 95%, at least about 1-fold, at least about 2-fold, at least about 3-fold, at least about 4-fold, at least about 5-fold, at least about 6-fold, or more.

After the compressed silk fibroin matrix is released from a delivery applicator (e.g., an injection applicator) and is placed (e.g., injected) into a tissue, the silk fibroin matrix can expand in response to the removal of the compressive stress, the size of a void in the tissue, the mechanical properties of the tissue and the silk fibroin matrix, and any combinations thereof. In some embodiments, the compressed silk fibroin matrix can expand and restore the original volume of the silk fibroin matrix the volume of the silk fibroin matrix before compression). In some embodiments, the compressed silk fibroin matrix can expand to a size sufficient to fill a void in the tissue to be repaired or augmented. In some embodiments, the silk fibroin matrix can expand to a size such that the silk fibroin matrix and the tissue surrounding the silk fibroin matrix are pressing each other with an equilibrium force. In certain embodiments, the compressed silk fibroin matrix can expand, upon placement (e.g., injection) into a tissue to be repaired or augmented, to a size in volume of at least about 10%, at least about 20%, at least about 30%, at least about 40%, at least about 50%, at least about 60%, at least about 70%, at least about 80%, at least about 90%, at least about 95%, or up to and including 100% of the original volume (i.e., the volume of the silk fibroin matrix before compression). In some embodiments, the compressed silk fibroin matrix can expand in volume upon placement (e.g., injection) into a tissue to be repaired or augmented, by at least about 1-fold, at least about 1.5-fold, at least about 2-fold, at least about 2.5-fold, at least about 3-fold, at least about 4-fold, at least about 5-fold, at least about 6-fold or higher, as compared to the compressed volume (e.g., the volume of the silk fibroin matrix being compressed inside a delivery applicator, e.g., an injection applicator, e.g., a needle, a cannula or a catheter). In such embodiments, without wishing to be bound by theory, the silk fibroin matrix can expand beyond its original volume, partly because the silk fibroin matrix can absorb moisture or water from the surrounding tissue, causing it to swell.

In some embodiments, stated another way, the compressed silk fibroin matrix can expand in volume by at least about 30%, at least about 40%, at least about 50%, at least about 60%, at least about 70%, at least a about 80%, at least about 90%, at least about 95%, at least about 1-fold, at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, at least about 10-fold, or more, relative to the volume of the compressed silk fibroin matrix.

The expansion of the silk fibroin matrix within the tissue to reach a plateau volume can be spontaneous (e.g., within 5 seconds or less) or occur over a period of time, e.g., seconds, minutes, and hours. In some embodiments, at least about 50% of the increase in volume of the silk fibroin matrix can occur in less than 3 hours, less than 2 hours, less than 1 hour, less than 30 mins, less than 20 mins, less than 10 mins, less than 5 minutes or shorter, upon injection of the silk fibroin matrix into the tissue, while the remaining increase in volume of the silk fibroin matrix can occur over a much longer time scale. The expansion rate of the silk fibroin matrix within the tissue can depend on several factors, including, but not limited to, hydration state, pressure, and volume of void space, as well as silk material properties, foam structural properties (including porosity), and interaction between the fluid and structure. For example, if the silk fibroin matrix (e.g., silk fibroin foam) is injected into a fluid-filled void, the expansion can be rapid. If a dry silk fibroin matrix (e.g., a dry silk fibroin foam) is injected, much slower hydration and expansion is likely to occur, e.g., from minutes to an hour.

After the silk fibroin matrix expands upon injection into the tissue, the silk fibroin matrix can retain at least a portion (e.g., at least about 50% or more) of its original expanded volume within the tissue for at least a period of time (e.g., at least about 2 weeks, at least about 4 weeks, at least about 6 weeks or longer).

By "original expanded volume" in reference to the silk fibroin matrix described herein is generally meant the volume of the silk fibroin matrix as measured after it has expanded upon injection within a tissue to be repaired or augmented, or the corresponding increase in tissue volume as measured after the silk fibroin matrix has expanded upon injection. For example, the original expanded volume of the silk fibroin matrix can be measured, for example, as soon as there is no significant increase in the volume of the silk fibroin matrix for at least about 72 hours, at least about 48 hours, at least about 24 hours, at least about 12 hours, at least about 6 hours, at least about 3 hours or less, upon injection of the silk fibroin matrix or the injectable composition into the tissue. Stated another way, the original expanded volume of the silk fibroin matrix can be determined by measuring the corresponding increase in tissue volume (due to the expansion of the silk fibroin matrix), as soon as there is no significant increase in the tissue volume for at least about 72 hours, at least about 48 hours, at least about 24 hours, at least about 12 hours, at least about 6 hours, at least about 3 hours or less, upon injection of the silk fibroin matrix or the injectable composition into the tissue. In some embodiments, the original expanded volume can refer to the original volume of the silk fibroin matrix (i.e., the volume of the silk fibroin matrix before compression).

As used herein, the term "retain" refers to maintaining the volume (e.g., size and/or shape) of the silk fibroin matrix described herein over a period of time. In some embodiments, the silk fibroin matrix can retain over a period of time at least about 20% of its original expanded volume, including, for example, at least about 30%, at least about 40%, at least about 50%, at least about 60%, at least about 70%, at least about 80%, at least about 90% of its original expanded volume or higher. In some embodiments, the silk fibroin matrix can retain over a period of time at least about 1% of its original expanded volume, including, for example, at least about 3%, at least about 5%, at least about 10%, at least about 15%, at least about 20% of its original expanded volume or higher. In some embodiments, the silk fibroin matrices can retain 100% of its original expanded volume, e.g., no detectable changes in the volume, within the tissue to be repaired or augmented for a period of time. In one embodiment, the silk fibroin matrix can retain at least about 1% of its original expanded volume within the tissue to be repaired or augmented for a period of time. In one embodiment, the silk fibroin matrix can retain at least about 50% of its original expanded volume within the tissue to be repaired or augmented for a period of time. In one embodiment, the silk fibroin matrix can retain at least about 60% of its original expanded volume within the tissue to be repaired or augmented for a period of time. In one embodiment, the silk fibroin matrix can retain at least about 70% of its original expanded volume within the tissue to be repaired or augmented for a period of time. In one embodiment, the silk fibroin matrix can retain at least about 80% of its original expanded volume within the tissue to be repaired or augmented for a period of time. The volume of the silk fibroin matrix placed into a tissue can be determined or indicated by a change in at least one of the tissue properties, e.g., tissue volume, tissue elasticity, and/or tissue hardness. In some embodiments, the volume of the silk fibroin matrix placed into a tissue can be determined from explants.

The silk fibroin matrix can retain at least a portion of its original expanded volume for any period of time, e.g., weeks, months, or years. In some embodiments, the silk fibroin matrix can retain, e.g., at least about 1% of its original expanded volume (including e.g., at least about 3%, at least about 5%, at least about 10%, at least about 15%, at least about 20%, at least about 30%, at least about 40%, at least about 50%, at least about 60%, at least about 70%, at least about 80%, or higher, of their original volume) for at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 1 year, at least about 2 years, at least 3 years, at least about 4 years, at least 5 years or longer. In certain embodiments, the silk fibroin matrix can retain, e.g., at least about 70% of its original expanded volume or higher, for at least about 3 months or longer. In other embodiments, there can be no significant changes in the volume of the silk fibroin matrix or the corresponding increase in tissue volume after placed into a tissue to be repaired or augmented for at least about 3 months or longer. In some embodiments, the silk fibroin matrix can retain, e.g., at least about 70% of its original expanded volume or higher, for at least about 6 months or longer (including, e.g., at least about 9 months, at least about 12 months, at least about 18 months or longer). In other embodiments, there can be no significant changes in the volume of the silk fibroin matrix or the corresponding increase in tissue volume after placed into a tissue to be repaired or augmented for at least about 6 months or longer. In particular embodiments, the silk fibroin matrix can retain at least about 20% of its original expanded volume or higher for at least about 1 year or longer (including, e.g., at least about 2 years, at least about 3 years, at least about 4 years, at least about 5 years or longer). In some embodiments, the silk fibroin matrix can retain at least about 50% of its original expanded volume or higher for at least about 1 year or longer (including, e.g., at least about 2 years, at least about 3 years, at least about 4 years, at least about 5 years or longer). In some embodiments, the silk fibroin matrix can retain at least about 1% of its original expanded volume or higher for at least about 1 year or longer (including, e.g., at least about 2 years, at least about 3 years, at least about 4 years, at least about 5 years or longer).

The volume retention of the silk fibroin matrix can also be characterized by, e.g., degradation of the silk fibroin matrix. Generally, the slower the silk fibroin matrix degrades, the longer the silk fibroin matrix can retain its original expanded volume in a tissue. Accordingly, some embodiments provided herein are directed to injectable compositions for use in repairing or augmenting a tissue in a subject, the compositions comprising a compressed silk fibroin matrix, wherein the compressed silk fibroin matrix expands upon injection into the tissue, and the silk fibroin matrix is adapted to degrade within the tissue to be repaired or augmented over a period of time.

As used in reference to the silk fibroin matrix described herein, the term "degrade" or "degradation" refers to a decrease in volume or size of the silk fibroin matrix. The degradation of the silk fibroin matrix can occur via cleavage of the silk fibroin matrix into smaller fragments and/or dissolution of the silk fibroin matrix or fragments thereof. In some embodiments, the silk fibroin matrix can be adapted to degrade no more than 80% of its original expanded volume, including, for example, no more than 70%, no more than 60%, no more than 50%, no more than 40%, no more than 30%, no more than 20%, no more than 10% of its original expanded volume or lower. In some embodiments, the silk fibroin matrix can exhibit no significant degradation (e.g., no detectable changes in the volume) within the tissue to be repaired or augmented. In one embodiment, the silk fibroin matrix can be adapted to degrade no more than 50% of its original expanded volume within the tissue to be repaired or augmented for a period of time. In one embodiment, the silk fibroin matrix can be adapted to degrade no more than 40% of its original expanded volume within the tissue to be repaired or augmented for a period of time. In one embodiment, the silk fibroin matrix can be adapted to degrade no more than 30% of its original expanded volume within the tissue to be repaired or augmented for a period of time. In one embodiment, the silk fibroin matrix can be adapted to degrade no more than 20% of its original expanded volume within the tissue to be repaired or augmented for a period of time. In one embodiment, the silk fibroin matrix can be adapted to degrade no more than 10% of its original expanded volume within the tissue to be repaired or augmented for a period of time.

In some embodiments, the silk fibroin matrix can be adapted to degrade at a pre-determined rate such that the original expanded volume of the silk fibroin matrix gradually decreases (while still providing sufficient support) as a tissue placed with the silk fibroin matrix begins to regenerate. In such embodiments, the silk fibroin matrix can be adapted to degrade at least about 5% of its original expanded volume, for example, including at least about 10%, at least about 20%, at least about 30%, at least about 40%, at least about 50%, at least about 60%, at least about 70%, at least about 80%, at least about 90%, at least about 95% or more, of its original expanded volume over a pre-determined period of time (e.g., a period of at least about 2 weeks, including at least about 6 weeks, at least about 3 months, at least about 6 months or longer.)

The silk fibroin matrix can be adapted to degrade at any rate. In some embodiments, the silk fibroin matrix can be adapted to degrade at least a portion of its original expanded volume over any period of time, e.g., weeks, months, or years. In some embodiments, the silk fibroin matrix can be adapted to degrade at least a portion of its original expanded volume, e.g., no more than 50% of its original expanded volume (including e.g., no more than 40%, no more than 30%, no more than 20% or lower, of its original expanded volume), in at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 1 year, at least about 2 years, at least about 3 years, at least about 4 years, at least about 5 years or longer. In certain embodiments, the silk fibroin matrix can be adapted to degrade, e.g., no more than 30% of its original expanded volume or lower, in at least about 3 months or longer. In other embodiments, there can be no significant degradation (i.e., no detectable changes in the volume of the silk fibroin matrix) after placed into a tissue to be repaired or augmented for at least about 3 months or longer. In some embodiments, the silk fibroin matrix can be adapted to degrade, e.g., no more than 30% of its original expanded volume or lower, in at least about 6 months or longer (including, e.g., at least about 9 months, at least about 12 months, at least about 18 months or longer). In other embodiments, there can be no significant degradation (i.e., no detectable changes in the volume of the silk fibroin matrix) after placed into a tissue to be repaired or augmented for at least about 6 months or longer. In particular embodiments, the silk fibroin matrix can be adapted to degrade no more than 80% of its original expanded volume or lower in at least about 1 year or longer (including, for example, at least about 2 years, at least about 3 years, at least about 4 years, at least about 5 years or longer). In some embodiments, the silk fibroin matrix can be adapted to degrade no more than 50% of its original expanded volume or lower in at least about 1 year or longer.

The same or similar formulation of the silk fibroin matrix or injectable compositions can manifest different responses in a subject. By way of example only, the volume retention or degradation rate of the silk fibroin matrix in a tissue can vary from one subject to another, e.g., because of different tissue microenvironment such as species and/or levels of various proteins or enzymes (e.g., proteolytic enzymes) present in the tissue.

In some embodiments, the silk fibroin matrix can be adapted to maintain a constant volume retention rate and/or degradation rate over a period of time. In some embodiments, the silk fibroin matrix can be adapted to have a volume retention rate or degradation rate varying with time. For example, the silk fibroin matrix can be coated with a polymeric material or a biomaterial, e.g., silk fibroin of a different concentration and/or a different biodegradable and biocompatible polymer. Such coating can possess a different function and/or a different degradation rate from that of the silk fibroin matrix core. By way of example only, the coating of the silk fibroin matrix can contain at least one active agent and be adapted to degrade at a different rate (e.g., at a faster rate) from that of the silk fibroin matrix core. Thus, upon placing the silk fibroin matrix in a tissue, the coating of the silk fibroin matrix can be adapted to degrade faster, e.g., to release the active agent for relieving the pain and/or promoting the wound healing, while the core of the silk fibroin matrix can retain their volume for a longer period of time.

Silk fibroin is a particularly appealing biopolymer candidate to be used for embodiments described herein, e.g., because of its versatile processing e.g., all-aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk has been approved by U.S. Food and Drug Administration as a tissue engineering scaffold in human implants. See Altman et al., 24 Biomaterials: 401 (2003).

As used herein, the term "silk fibroin" includes silkworm fibroin and insect or spider silk protein. See e.g., Lucas et al., 13 Adv. Protein Chem. 107 (1958). Any type of silk fibroin can be used in different embodiments described herein. Silk fibroin produced by silkworms, such as *Bombyx mori*, is the most common and represents an earth-friendly, renewable resource. For instance, silk fibroin used in a silk film may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments, silk fibroin can be derived from other sources such as spiders, other silkworms, bees, and bioengineered variants thereof.

In various embodiments, the silk fibroin can be modified for different applications and/or desired mechanical or chemical properties (e.g., to facilitate formation of a gradient of active agent in silk fibroin matrices). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No. WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. Additionally, the silk fibroin matrix can be combined with a chemical, such as glycerol, that, e.g., affects flexibility of the matrix. See, e.g., WO 2010/042798, Modified Silk films Containing Glycerol.

As used interchangeably herein, the phrase "silk fibroin matrix" or "silk fibroin-based matrix" generally refer to a matrix comprising silk fibroin. In some embodiments, the phrases "silk fibroin matrix" and "silk fibroin-based matrix" refer to a matrix in which silk fibroin constitutes at least about 30% of the total composition, including at least about 40%, at least about 50%, at least about 60%, at least about 70%, at least about 80%, at least about 90%, at least about 95% or higher, of the total composition. In certain embodiments, the silk fibroin matrix or the silk fibroin-based matrix can be substantially formed from silk fibroin. In various embodiments, the silk fibroin matrix or the silk fibroin-based matrix can be substantially formed from silk fibroin comprising at least one active agent. In some embodiments, the silk fibroin matrix or silk fibroin-based matrix can refer to a silk fibroin foam or a silk fibroin-based foam.

The silk fibroin matrix described herein can be adapted to be any shape, e.g., a spherical shape, polygonal-shaped, elliptical-shaped, cylindrical-shaped, tubular-shaped, or any art-recognized shapes. The size of the silk fibroin matrix can vary with a number of factors including, without limitations, the size of the tissue to be repaired or augmented and/or desired properties of the silk fibroin matrix, e.g., volume retention or degradation profile. In some embodiments, the silk fibroin matrix (prior to compression) can have a size of about 1 mm to about 5 mm in diameter. In some embodiments, the silk fibroin matrix (prior to compression) can have a size larger than 5 mm in diameter. Since the silk fibroin matrix are compressible or deformable, the size of the silk fibroin matrix can be as large as feasible to fill larger sized defects as long as the size of the compressed silk fibroin matrix is feasible for injection into a tissue.

The silk fibroin matrices can be produced from aqueous-based or organic solvent-based silk fibroin solutions. In some embodiments, the silk fibroin matrices produced from organic solvent-based silk fibroin solution can retain their original volume for a longer period of time than the aqueous-based silk fibroin matrices. The aqueous- or organic solvent-based silk fibroin solution used for making silk fibroin matrices described herein can be prepared using any techniques known in the art. The concentration of silk fibroin in solutions used for soft tissue repair or augmentation can be suited to the particular volume retention requirement, e.g., if higher concentrations of silk fibroin solutions can be used when longer volume retention of the silk fibroin matrices is desired when injected into the tissue to be repaired or augmented. In some embodiments, the silk fibroin solution for making the silk fibroin matrices described herein can vary from about 0.1% (w/v) to about 30% (w/v), inclusive. In some embodiments, the silk fibroin solution can vary from about 0.5% (w/v) to about 10% (w/v). In some embodiments, the silk fibroin solution can vary from about 1% (w/v) to about 6% (w/v). Suitable processes for preparing silk fibroin solution are disclosed, for example, in U.S. Pat. No. 7,635,755; and International Application Nos.

WO/2005/012606; and WO/2008/127401. A micro-filtration step can be used herein. For example, the prepared silk fibroin solution can be processed further, e.g., by centrifugation and/or syringe based micro-filtration before further processing into silk fibroin matrices described herein.

In some embodiments, the silk fibroin can be also mixed with other biocompatible and/or biodegradable polymers to form mixed polymer matrices comprising silk fibroin. One or more biocompatible and/or biodegradable polymers (e.g., two or more biocompatible polymers) can be added to the silk fibroin solution. The biocompatible polymer that can be used herein include, but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible and/or biodegradable polymers. See, e.g., International Application Nos. WO 04/062697; WO 05/012606.

In some embodiments, at least one active agent described herein can be added to the silk fibroin solution before further processing into silk fibroin matrices described herein. In some embodiments, the active agent can be dispersed homogeneously or heterogeneously within the silk fibroin, dispersed in a gradient, e.g., using the carbodiimide-mediated modification method described in the U.S. Patent Application No. US 2007/0212730.

In some embodiments, the silk fibroin matrices can be first formed and then contacted with (e.g., dipped into) at least one active agent such that the open surface of the matrices can be coated with at least one active agent.

In some embodiments, the silk fibroin matrices described herein can comprise porous structures, e.g., to mimic the structural morphology of a native tissue, to modulate the degradation rate/volume retention rate of the silk fibroin matrices, and/or to modulate release profile of an active agent embedded therein, if any. As used herein, the terms "porous" and "porosity" are generally used to describe a structure having a connected network of pores or void spaces (which can, for example, be openings, interstitial spaces or other channels) throughout its volume. The term "porosity" is a measure of void spaces in a material, and is a fraction of volume of voids over the total volume, as a percentage between 0 and 100% (or between 0 and 1).

In some embodiments, the porous silk fibroin matrices can be configured to have any porosity, depending on the desired properties. For example, in some embodiments, the porous silk fibroin matrix can have a porosity of at least about 1%, at least about 3%, at least about 5%, at least about 10%, at least about 15%, at least about 20%, at least about 25%, at least about 30%, at least about 40%, at least about 50%, at least about 60%, at least about 70%, at least about 80%, at least about 90% or higher. In some embodiments, the porosity can range from about 70% to about 99%, or from about 80% to about 98%. The pore size and total porosity values can be quantified using conventional methods and models known to those of skill in the art. For example, the pore size and porosity can be measured by standardized techniques, such as mercury porosimetry and nitrogen adsorption. One of ordinary skill in the art can determine the optimal porosity of the silk fibroin matrices for various purposes. For example, the porosity and/or pore size of the silk fibroin matrices can be optimized based on the desired degradation rate or volume retention rate of the silk fibroin matrices, release profiles of an active agent from the silk fibroin matrices, and/or the structural morphology of the tissue to be repaired or augmented.

The pores can be adapted to have any shape, e.g., circular, elliptical, or polygonal. The porous silk fibroin matrices can be adapted to have a pore size of about 1 μm to about 1500 μm, about 10 μm to about 1000 μm, about 25 μm to about 800 μm, about 50 μm to about 650 μm, or about 100 μm to about 600 μm. In some embodiments, the pores can have a size of about 100 μm to about 600 μm. In some embodiments, the silk fibroin matrix can have a pore size of less than 1 μm. In other embodiments, the silk fibroin matrix needs not be porous. In such embodiments, the pore size of the silk fibroin matrix can be less than 10 nm or non-detectable. The term "pore size" as used herein refers to a dimension of a pore. In some embodiments, the pore size can refer to the longest dimension of a pore, e.g., a diameter of a pore having a circular cross section, or the length of the longest cross-sectional chord that can be constructed across a pore having a non-circular cross-section. In other embodiments, the pore size can refer the shortest dimension of a pore.

Methods for generating porous structures within silk fibroin matrix, e.g., freeze-drying, porogen-leaching method (e.g., salt-leaching), and gas foaming methods, are well known in the art and have been described in, e.g., U.S. Pat. No. 7,842,780; and US Patent Application Nos. US 2010/0279112; and US 2010/0279112, the contents of which are incorporated herein by reference in their entirety.

In some embodiments, the porous silk fibroin matrices are not produced by a porogen-leaching method (e.g., salt-leaching method) as described in, e.g., U.S. Pat. No. 7,842,780; and US 2010/0279112.

In some embodiments, porous silk fibroin matrices can be produced by freeze-drying method. See, e.g., U.S. Pat. No. 7,842,780, and US 2010/0279112. In such embodiments, the silk fibroin solution placed in a non-stick container can be frozen at sub-zero temperatures, e.g., from about −80° C. to about −20° C., for at least about 12 hours, at least about 24 hours, or longer, followed by lyophilization. In one embodiment, the silk fibroin solution can be frozen from one direction. In some embodiments, the silk fibroin solution can contain no salt. In some embodiments, alcohol such as 15%-25% of methanol or propanol can be added to the silk fibroin solution.

In certain embodiments, porous silk fibroin matrices can be produced by freezing the silk fibroin solution at a temperature range between about −1° C. and about −20° C. or between about −5° C. and −10° C., for at least about 2 days, at least about 3 days or longer, followed by lyophilization for at least about 2 days, at least about 3 days or longer. See, e.g., U.S. 61/477,486. The freezing temperature and/or duration, and/or lyophilization duration can be adjusted to generate a silk fibroin matrix of different porous structures and/or mechanical properties.

In some embodiments, the silk fibroin solution can be exposed to an electric field, e.g., by applying a voltage to the silk fibroin solution. The silk fibroin solution that did not change to a gel after exposure to an electric field can then be placed in a freezer for an extended period of time, e.g., at least about 1 day, at least about 2 days, at least about 3 days, at least about 5 days, at least about 6 days or longer. The frozen silk fibroin matrix can then be removed from the freezer and stored at about room temperature, resulting in a silk fibroin matrix of various porous structures and/or properties.

In some embodiments, silk fibroin matrices described herein can be subjected to a post-treatment that will affect at least one silk fibroin property. For example, post-treatment of silk fibroin matrices can affect silk fibroin properties including β-sheet content, solubility, active agent loading capacity, degradation time, drug permeability or any combinations thereof. Silk post-processing options include controlled slow drying (Lu et al., 10 Biomacromolecules 1032 (2009)), water annealing (Jin et al., Water-Stable Silk Films with Reduced β-Sheet Content, 15 Adv. Funct. Mats. 1241 (2005)), stretching (Demura & Asakura, Immobilization of glucose oxidase with *Bombyx mori* silk fibroin by only stretching treatment and its application to glucose sensor, 33 Biotech & Bioengin. 598 (1989)), compressing, and solvent immersion, including methanol (Hofmann et al., 2006), ethanol (Miyairi et al., 1978), glutaraldehyde (Acharya et al., 2008) and 1-ethyl-3-(3-dimethyl aminopropyl) carbodiimide (EDC) (Bayraktar et al., 2005).

In some embodiments, post-treatment of the silk fibroin matrices, e.g., water-annealing or solvent immersion, can allow controlling the release of an active agent from the silk fibroin matrices. In some embodiments, post-treatment of the silk fibroin matrices, e.g., water-annealing or solvent immersion, can enable modulating the degradation or solubility properties of the silk fibroin matrices used in the methods described herein. In some embodiments, post-treatment of the silk fibroin matrices, e.g., water-annealing or solvent immersion, can enable modulating the volume retention properties of the silk fibroin matrices used in the methods described herein.

In some embodiments, the silk fibroin matrices described herein can be coated with at least one layer of a biocompatible and/or biodegradable polymer described herein, e.g., to modulate the degradation and/or volume retention properties of the fibroin matrices upon injection into a tissue to be treated and/or to modulate the rate of active agents released from the silk fibroin matrices. In such embodiments, the biocompatible and/or biodegradable polymer can comprise at least one active agent.

In some embodiments, the silk fibroin matrices described herein can be coated with cell adhesion molecules, e.g., but not limited to, fibronectin, vitronectin, laminin, collagen, any art-recognized extracellular matrix molecules, and any combinations thereof.

In some embodiments, the silk fibroin matrices described herein can be sterilized. Sterilization methods for biomedical devices are well known in the art, including, but not limited to, gamma or ultraviolet radiation, autoclaving (e.g., heat/steam); alcohol sterilization (e.g., ethanol and methanol); and gas sterilization (e.g., ethylene oxide sterilization).

Further, the silk fibrin matrices described herein can take advantage of the many techniques developed to functionalize silk fibroin (e.g., active agents such as dyes and sensors). See, e.g., U.S. Pat. No. 6,287,340, Bioengineered anterior cruciate ligament; WO 2004/000915, Silk Biomaterials & Methods of Use Thereof; WO 2004/001103, Silk Biomaterials & Methods of Use Thereof; WO 2004/062697, Silk Fibroin Materials & Use Thereof; WO 2005/000483, Method for Forming inorganic Coatings; WO 2005/012606, Concentrated Aqueous Silk Fibroin Solution & Use Thereof; WO 2011/005381, Vortex-Induced Silk fibroin Gelation for Encapsulation & Delivery; WO 2005/123114, Silk-Based Drug Delivery System; WO 2006/076711, Fibrous Protein Fusions & Uses Thereof in the Formation of Advanced Organic/Inorganic Composite Materials; U.S. Application Pub. No. 2007/0212730, Covalently immobilized protein gradients in three-dimensional porous scaffolds; WO 2006/042287. Method for Producing Biomaterial Scaffolds; WO 2007/016524, Method for Stepwise Deposition of Silk Fibroin Coatings; WO 2008/085904, Biodegradable Electronic Devices; WO 2008/118133, Silk Microspheres for Encapsulation & Controlled Release; WO 2008/108838, Microfluidic Devices & Methods for Fabricating Same; WO 2008/127404, Nanopatterned Biopolymer Device & Method of Manufacturing Same; WO 2008/118211, Biopolymer Photonic Crystals & Method of Manufacturing Same; WO 2008/127402, Biopolymer Sensor & Method of Manufacturing Same; WO 2008/127403, Biopolymer Optofluidic Device & Method of Manufacturing the Same; WO 2008/127401, Biopolymer Optical Wave Guide & Method of Manufacturing Same; WO 2008/140562, Biopolymer Sensor & Method of Manufacturing Same; WO 2008/127405, Microfluidic Device with Cylindrical Microchannel & Method for Fabricating Same; WO 2008/106485, Tissue-Engineered Silk Organs; WO 2008/140562, Electroactive Biopolymer Optical & Electro-Optical Devices & Method of Manufacturing Same; WO 2008/150861, Method for Silk Fibroin Gelation Using Sonication; WO 2007/103442, Biocompatible Scaffolds & Adipose-Derived Stem Cells; WO 2009/155397, Edible Holographic Silk Products; WO 2009/100280, 3-Dimensional Silk Hydroxyapatite Compositions; WO 2009/061823, Fabrication of Silk Fibroin Photonic Structures by Nanocontact Imprinting; WO 2009/126689, System & Method for Making Biomaterial Structures.

In an alternative embodiment, the silk fibroin matrices can include plasmonic nanoparticles to form photothermal elements. This approach takes advantage of the superior doping characteristics of silk fibroin. Thermal therapy has been shown to aid in the delivery of various agents, see Park et al., Effect of Heat on Skin Permeability, 359 Intl. J. Pharm. 94 (2008). In one embodiment, short bursts of heat on very limited areas can be used to maximize permeability with minimal harmful effects on surrounding tissues. Thus, plasmonic particle-doped silk fibroin matrices can add specificity to thermal therapy by focusing light to locally generate heat only via the silk fibroin matrices. In some embodiments, the silk fibroin matrices can include photothermal agents such as gold nanoparticles.

In some embodiments, the silk fibroin matrices used in the methods described herein can include an amphiphilic peptide. In other embodiments, the silk fibroin matrices used in the methods described herein can exclude an amphiphilic peptide. "Amphiphilic peptides" possess both hydrophilic and hydrophobic properties. Amphiphilic molecules can generally interact with biological membranes by insertion of the hydrophobic part into the lipid membrane, while exposing the hydrophilic part to the aqueous environment. In some embodiment, the amphiphilic peptide can comprise a RGD motif. An example of an amphiphilic peptide is a 23RGD peptide having an amino acid sequence: HOOC-Gly-Arg-Gly-Asp-Ile-Pro-Ala-Ser-Ser-Lys-Gly-Gly-Gly-Gly-Ser-rArg-Leu-Leu-Leu-Leu-Leu-Leu-Arg-NH2. Other examples of amphiphilic peptides include the ones disclosed in the U.S. Patent App. No. US 2011/0008406.

Injectable Compositions Comprising a Silk Fibroin Matrix

In another aspect, provided herein is an injectable composition for use in repairing or augmenting a tissue in a subject comprising a compressed silk fibroin matrix, wherein the compressed silk fibroin matrix expands upon injection into the tissue, and retains its original expanded volume (e.g., at least about 50% or higher) within the tissue to be repaired or augmented for a period of time (e.g., at least about 2 weeks, at least about 4 weeks, at least about 6 weeks or longer).

As used herein, the term "injectable composition" generally refers to a composition that can be delivered or administered into a tissue with a minimally invasive procedure. The term "minimally invasive procedure" refers to a procedure that is carried out by entering a subject's body through the skin or through a body cavity or an anatomical opening, but with the smallest damage possible (e.g., a small incision, injection). In some embodiments, the injectable composition can be administered or delivered into a tissue by injection. In some embodiments, the injectable composition can be delivered into a tissue through a small incision on the skin followed by insertion of a needle, a cannula and/or tubing, e.g., a catheter. Without wishing to be limited, the injectable composition can be administered or placed into a tissue by surgery, e.g., implantation.

In some embodiments, the injectable compositions can comprise at least one active agent described herein.

In some embodiments, the injectable composition can comprise at least one cell. The term "cells" used herein refers to any cell, prokaryotic or eukaryotic, including plant, yeast, worm, insect and mammalian. In some embodiments, the cells can be mammalian cells. Mammalian cells include, without limitation; primate, human and a cell from any animal of interest, including without limitation; mouse, rat, hamster, rabbit, dog, cat, domestic animals, such as equine, bovine, murine, ovine, canine, feline, etc. The cells can be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoietic, neural, stromal, muscle, cardiovascular, hepatic, pulmonary, and gastrointestinal stem cells and adipose-derived stem cells. In one embodiment, the cells are adipose-derived stem cells. In some embodiments, the cells can be ex vivo or cultured cells, e.g. in vitro. For example, for ex vivo cells, cells can be obtained from a subject, where the subject is healthy and/or affected with a disease. Cells can be obtained, as a non-limiting example, by biopsy or other surgical means known to those skilled in the art. In some embodiments, adipose cells can be harvested from a subject by conventional liposuction or aspiration techniques. In such embodiments, the cells can be derived from a lipoaspirate. In other embodiments, the cells can be derived from a bone-marrow aspirate. Depending on the types of tissues to be repaired or augmented, cells can be derived from any biological fluid or concentrate, e.g., a lipoaspirate or a bone-marrow lipoaspirate. In some embodiments, the injectable composition or the silk fibroin matrix can be directly delivered with a biological fluid or concentrate, e.g., a lipoaspirate or a bone-marrow aspirate.

Cells can be obtained from donors (allogenic) or from recipients (autologous). Cells can also be of established cell culture lines, or even cells that have undergone genetic engineering. Additionally, cells can be collected from a multitude of hosts including but not limited to human autograft tissues, transgenic mammals, or bacterial cultures (possibly for use as a probiotic treatment). In certain embodiments, the injectable compositions and/or silk fibroin matrices can comprise human stem cells such as, e.g., mesenchymal stem cells, induced pluripotent stein cells (iPSCs), synovial derived stem cells, embryonic stem cells, adult stem cells, umbilical cord blood cells, umbilical Wharton's jelly cells, osteocytes, fibroblasts, neuronal cells, lipocytes, adipocytes, bone marrow cells, assorted immunocytes, precursor cells derived from adipose tissue, bone marrow derived progenitor cells, peripheral blood progenitor cells, stem cells isolated from adult tissue and genetically transformed cells or combinations of the above cells; or differentiated cells such as, e.g., muscle cells, adipose cells.

Stem cells can be obtained with minimally invasive procedures from bone marrow, adipose tissue, or other sources in the body, are highly expandable in culture, and can be readily induced to differentiate into adipose tissue forming cells after exposure to a well-established adipogenic inducing supplement. Cells can be added to the injectable compositions and/or silk fibroin matrices described herein and cultured in vitro for a period of time prior to administration to a region of the body, or added to injectable compositions and/or silk fibroin matrices described herein and administered into a region of the body. The cells can be seeded on the silk fibroin matrices for a short period of time (less than 1 day) just prior to administration, or cultured for a longer (more than 1 day) period to allow for cell proliferation and extracellular matrix synthesis within the seeded matrix prior to administration.

When utilized as a source of stem cells, adipose tissue can be obtained by any method known to a person of ordinary skill in the art. For example, adipose tissue can be removed from an individual by suction-assisted lipoplasty, ultrasound-assisted lipoplasty, and excisional lipectomy. In addition, the procedures can include a combination of such procedures. Suction assisted lipoplasty can be desirable to remove the adipose tissue from an individual as it provides a minimally invasive method of collecting tissue with minimal potential for stem cell damage that can be associated with other techniques, such as ultrasound assisted lipoplasty. The adipose tissue should be collected in a manner that preserves the viability of the cellular component and that minimizes the likelihood of contamination of the tissue with potentially infectious organisms, such as bacteria and/or viruses.

In some embodiments, preparation of the cell population can require depletion of the mature fat-laden adipocyte component of adipose tissue. This is typically achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix. Disaggregation can be achieved using any conventional techniques or methods, including mechanical force (mincing or shear forces), enzymatic digestion with single or combinatorial proteolytic enzymes, such as collagenase, trypsin, lipase, liberase HI and pepsin, or a combination of mechanical and enzymatic methods. For example, the cellular component of the intact tissue fragments can be disaggregated by methods using collagenase-mediated dissociation of adipose tissue, similar to the methods for collecting microvascular endothelial cells in adipose tissue, as known to those of skill in the art. Additional methods using collagenase that can be used are also known to those of skill in the art. Furthermore, methods can employ a combination of enzymes, such as a combination of collagenase and trypsin or a combination of an enzyme, such as trypsin, and mechanical dissociation.

The cell population (processed lipoaspirate) can then be obtained from the disaggregated tissue fragments by reducing the presence of mature adipocytes. Separation of the cells can be achieved by buoyant density sedimentation, centrifugation, elutriation, differential adherence to and elution from solid phase moieties, antibody-mediated selection, differences in electrical charge; immunomagnetic beads, fluorescence activated cell sorting (FACS), or other means.

Following disaggregation the active cell population can be washed/rinsed to remove additives and/or by-products of the disaggregation process (e.g., collagenase and newly released free lipid). The active cell population could then be concentrated by centrifugation. In one embodiment, the cells are concentrated and the collagenase removed by passing the cell population through a continuous flow spinning membrane system or the like, such as, for example, the system disclosed in U.S. Pat. Nos. 5,034,135; and 5,234,608, which are incorporated by reference herein.

In addition to the foregoing, there are many post-wash methods that can be applied for further purifying the cell population. These include both positive selection (selecting the target cells), negative selection (selective removal of unwanted cells), or combinations thereof. In another embodiment the cell pellet could be resuspended, layered over (or under) a fluid material formed into a continuous or discontinuous density gradient and placed in a centrifuge for separation of cell populations on the basis of cell density. In a similar embodiment, continuous flow approaches such as apheresis and elutriation (with or without countercurrent) could be used. Adherence to plastic followed by a short period of cell expansion has also been applied in bone marrow-derived adult stern cell populations. This approach uses culture conditions to preferentially expand one population while other populations are either maintained (and thereby reduced by dilution with the growing selected cells) or lost due to absence of required growth conditions. The cells that have been concentrated, cultured and/or expanded can be incorporated into the silk fibroin matrices and/or injectable compositions described herein.

In one embodiment, stem cells are harvested, the harvested cells are contacted with an adipogenic medium for a time sufficient to induce differentiation into adipocytes, and the adipocytes are loaded onto a biocompatible matrix which is implanted. In additional embodiments, at least some of the stem cells can be differentiated into adipocytes so that a mixture of both cell types is initially present that changes over time to substantially only adipocytes, with stem cells being present in small to undetectable quantities. Adipose tissue is fabricated in vivo by the stem cells or prepared ex vivo by the stern cells.

A number of different cell types or combinations thereof can be employed in the injectable compositions, depending upon the types of tissues to be repaired or augmented. These cell types include, but are not limited to: smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. By way of example only, smooth muscle cells and endothelial cells can be employed when the injectable compositions are used to repair or augment muscular and/or vascular tissues, such as vascular, esophageal, intestinal, rectal, or ureteral tissues; chondrocytes can be included in injectable compositions for cartilaginous tissues; fibroblasts can be included in injectable compositions intended to replace and/or enhance any of the wide variety of tissue types (e.g., skin) that contains extracellular matrix, e.g., collagen; adipocytes can be included in injectable compositions intended to repair or augment any of the wide variety of adipose tissues, in general, any cells that are found in the natural tissue can be included in the injectable compositions used for corresponding tissue. In addition, progenitor cells, such as myoblasts or stem cells, can be included to produce their corresponding differentiated cell types.

In some embodiments, the injectable compositions can further comprise a pharmaceutically acceptable carrier. As used herein, the term "pharmaceutically acceptable carrier" refers to a pharmaceutically-acceptable material, composition or vehicle for administration of a silk fibroin matrix, and optionally an active agent. Pharmaceutically acceptable carriers include any and all solvents, dispersion media, coatings, antibacterial and antifungal agents, and isotonic and absorption delaying agents, which are compatible with the silk fibroin matrices and the activity of the active agent, if any, and are physiologically acceptable to the subject. The pharmaceutical formulations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

Additionally, various additives which enhance the stability, sterility, and isotonicity of the injectable compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it may be desirable to include isotonic agents, for example, sugars, sodium chloride, and the like. The injectable compositions can also contain auxiliary substances such as wetting or emulsifying agents, pH buffering agents, gelling or viscosity enhancing additives, preservatives, colors, and the like, depending upon the preparation desired. Standard texts, such as "REMINGTON'S PHARMACEUTICAL SCIENCE", 17th edition, 1985, incorporated herein by reference, may be consulted to prepare suitable preparations, without undue experimentation.

Viscosity of the injectable compositions can be maintained at the selected level using a pharmaceutically acceptable thickening agent. In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected, and the desired viscosity for injection. The important point is to use an amount which will achieve the selected viscosity, e.g., addition of such thickening agents into some embodiments of the injectable compositions.

Typically, any additives (in addition to the silk fibroin matrices described herein and/or additional active agents) can be present in an amount of 0.001 to 50 wt % dry weight or in a buffered solution. In some embodiments, the active agent can be present in the order of micrograms to milligrams to grams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any pharmaceutical composition to be administered to a subject in need thereof, it is preferred to determine toxicity, such as by determining the lethal dose (LD) and LD50 in a suitable animal model e.g., rodent such as mouse or rat; and, the dosage of the composition(s), concentration of components therein and timing of administering the composition(s), which elicit a suitable response. Such determinations do not require undue experimentation from the knowledge of the skilled artisan.

Active Agents

In some embodiments, the injectable composition and/or the silk fibroin matrices described herein can further comprise at least one active agent. The active agent can be mixed, dispersed, or suspended in the injectable composition, and/or it can be distributed or embedded in the silk fibroin matrices. In some embodiments, the active agent can be distributed, embedded or encapsulated in the silk fibroin matrices. In some embodiments, the active agent can be coated on surfaces of the silk fibroin matrices. In some embodiments, the active agent can be mixed with the silk fibroin matrices to form an injectable composition. The term "active agent" can also encompass combinations or mixtures of two or more active agents, as described below. Examples of active agents include, but are not limited to, a biologically active agent (e.g., a therapeutic agent), a cosmetically active agent (e.g., an anti-aging agent), a cell attachment agent (e.g., integrin-binding molecules), and any combinations thereof.

The term "biologically active agent" as used herein refers to any molecule which exerts at least one biological effect in vivo. For example, the biologically active agent can be a therapeutic agent to treat or prevent a disease state or condition in a subject. Examples of biologically active agents include, without limitation, peptides, peptidomimetics, aptamers, antibodies or a portion thereof, antibody-like molecules, nucleic acids (DNA, RNA, siRNA, shRNA), polysaccharides, enzymes, receptor antagonists or agonists, hormones, growth factors, autogenous bone marrow, antibiotics, antimicrobial agents, small molecules and therapeutic agents. The biologically active agents can also include, without limitations, anti-inflammatory agents, anesthetics, active agents that stimulate issue formation, and/or healing and regrowth of natural tissues, and any combinations thereof.

Anti-inflammatory agents can include, but are not limited to, naproxen, sulindac, tolmetin, ketorolac, celecoxib, ibuprofen, diclofenac, acetylsalicylic acid, nabumetone, etodolac, indomethacin, piroxicam, cox-2 inhibitors, ketoprofen, antiplatelet medications, salsalate, valdecoxib, oxaprozin, diflunisal, flurbiprofen, corticosteroids, MMP inhibitors and leukotriene modifiers or combinations thereof.

Agents that increase formation of new tissues and/or stimulates healing or regrowth of native tissue at the site of injection can include, but are not limited to, fibroblast growth factor (FGF), transforming growth factor-beta (TGF-β), platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

Anesthetics can include, but are not limited to, those used in caudal, epidural, inhalation, injectable, retrobulbar, and spinal applications, such as bupivacaine, lidocaine, benzocaine, cetacaine, ropivacaine, and tetracaine, or combinations thereof.

In some embodiments, the active agents can be cosmetically active agents. By the term "cosmetically active agent" is meant a compound that has a cosmetic or therapeutic effect on the skin, hair, or nails, e.g., anti-aging agents, anti-free radical agents, lightening agents, whitening agents, depigmenting agents, darkening agents such as self-tanning agents, colorants, anti-acne agents, shine control agents, anti-microbial agents, anti-inflammatory agents, anti-mycotic agents, anti-parasite agents, external analgesics, sun-blocking agents, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, muscle relaxants, agents for hair, nail, and/or skin conditioning, and any combination thereof.

In one embodiment, the cosmetically active agent can be selected from, but not limited to, the group consisting of hydroxy acids, benzoyl peroxide, sulfur resorcinol, ascorbic acid, D-panthenol, hydroquinone, octyl methoxycinnamate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, and soy, and derivatives and mixtures thereof. Examples of vitamins include, but are not limited to, vitamin A, vitamin Bs (such as vitamin B3, vitamin B5, and vitamin B12), vitamin C, vitamin K, and vitamin E, and derivatives thereof.

In one embodiment, the cosmetically active agents can be antioxidants. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions described herein can include, but are not limited to, butylated hydroxytoluene, tocopherols (e.g., tocopheryl acetate), tocotrienols, and ubiquinone. Natural extracts containing antioxidants suitable for use in the injectable compositions described herein can include, but not limited to, extracts containing flavonoids and isoflavonoids and their derivatives (e.g., genistein and diadzein), and extracts containing resveratrol. Examples of such natural extracts include grape seed, green tea, pine bark, and propolis. Other examples of antioxidants can be found on pages 1612-13 of the ICI Handbook.

In some embodiments, the active agents can be cell attachment agents. Examples of cell attachment agents include, but are not limited to, hyaluronic acid, collagen, crosslinked hyaluronic acid/collagen, an integrin-binding molecule, chitosan, elastin, fibronectin, vitronectin, laminin, proteoglycans, any derivatives thereof, any peptide or oligosaccharide variants thereof, and any combinations thereof. As used herein, the term "oligosaccharide" means a compound comprising at least two or more sugars, selected from the group consisting of glucose, fructose, galactose, xylose and any combinations thereof. In one embodiment, the oligosaccharide can be selected from the group consisting of fructooligosaccharide, galactooligosaccharide, lactosucrose, isomaltulose, glycosyl sucrose, isomaltooligosaccharide, gentioligosaccharide, xylooligosaccharide and any combinations thereof. As used herein, the term "oligosaccharides" includes disaccharides.

In some embodiments, the injectable compositions and/or silk fibroin matrices can further comprise at least one additional material for soft tissue augmentation, e.g., dermal filler materials, including, but not limited to, poly(methyl methacrylate) microspheres, hydroxylapatite, poly(L-lactic acid), collagen, gelatin, elastin, and glycosaminoglycans, hyaluronic acid, commercial dermal filler products such as BOTOX® (from Allergan), DYSPORT®, COSMODERM®, EVOLENCE®, RADIESSE®, RESTYLANE®, JUVEDERM® (from Allergan), SCULPTRA®, PERLANE®, and CAPTIQUE®, and any combinations thereof.

In some embodiments, the injectable composition and/or silk fibroin matrices can comprise metallic nanoparticles (e.g., but not limited to, gold nanoparticles), optical molecules (e.g., but not limited to, fluorescent molecules, and/or quantum dots), and any other art-recognized contrast agent, e.g., for biomedical imaging.

In various embodiments, the injectable compositions can be stored or transported dried or hydrated.

When the active agents are embedded in the silk fibroin matrices, the bioactivity of the active agents (e.g., at least about 30% of the bioactivity of the active agents) can be stabilized for a period of time (e.g., days, weeks, or months) under specific conditions. Such conditions can include, but are not limited to, a state-changing cycle (e.g., freeze-thaw cycles), temperatures (e.g., above 0° C.), air pressures, humidity, and light exposure. See U.S. Application Ser. No. 61/477,737. Some embodiments of the injectable composition can be stored or transported between about 0° C. and about 60° C., about 10° C. and about 60° C., or about 15° C. and about 60° C. In these embodiments, the injectable compositions can be stored or transported at room temperatures while the bioactivity of the active agents (e.g., at least about 30% of the bioactivity of the active agents) can be stabilized for a period of time, e.g., at least about 3 weeks or longer.

Applications of Injectable Compositions and Silk Fibroin Matrices Described Herein The injectable compositions described herein can be used in a variety of medical uses, including, without limitation, fillers for tissue space, templates for tissue reconstruction or regeneration, scaffolds for cells in tissue engineering applications, or as a vehicle/carrier for thug delivery. A silk fibroin matrix described herein injected into a tissue to be repaired or augmented can act as a scaffold to mimic the extracellular matrices (ECM) of the body, and/or promote tissue regeneration. The scaffold can serve as both a physical support and/or an adhesive template for cells to proliferate therein. In some embodiments, the silk fibroin matrix can contain no cells. Yet the silk fibroin matrix can be coated with cell attachment agents, e.g., collagen, and/or chemoattractants, e.g., growth factors, that can attract host cells to the silk fibroin matrix and support the cell proliferation. In some embodiments, the silk fibroin matrix can be seeded with cells prior to administration to a target tissue to be repaired or augmented.

In some embodiments, provided herein are injectable compositions that can be used to fill, volumize, and/or regenerate a tissue in need thereof. The injectable compositions can generally be used for tissue filling or volumizing, soft tissue augmentation, replacement, cosmetic enhancement and/or tissue repair in a subject. Additionally, the injectable compositions can be used for filling of any tissue void or indentation that are either naturally formed (e.g., aging) or created by surgical procedure for removal of tissue (e.g., a dermal cyst or a solid tumor), corticosteroid treatment, immunologic reaction resulting in lipoatrophy, tissue damage resulting from impact injuries or therapeutic treatment (e.g., radiotherapy or chemotherapy). The injectable compositions can also be used to raise scar depressions.

In certain embodiments, the injectable compositions can be used for soft tissue augmentation. As used herein, by the term "augmenting" or "augmentation" is meant increasing, filling in, restoring, enhancing or replacing a tissue. In some embodiments, the tissue can lose its elasticity, firmness, shape and/or volume. In some embodiments, the tissue can be partially or completely lost (e.g., removal of a tissue) or damaged. In those embodiments, the term "augmenting" or "augmentation" can also refer to decreasing, reducing or alleviating at least one symptom or defect in a tissue (for example, but not limited to, loss of elasticity, firmness, shape and/or volume in a tissue; presence of a void or an indentation in a tissue; loss of function in a tissue) by injecting into the tissue with at least one injectable composition described herein. In such embodiments, at least one symptom or defect in a tissue can be decreased, reduced or alleviated by at least about 30%, at least about 40%, at least about 50%, at least about 60%, at least about 70%, at least about 80% or higher, as compared to no treatment. In some embodiments, at least one symptom or defect in a tissue can be decreased, reduced or alleviated by at least about 90%, at least about 95%, at least about 97%, or higher, as compared to no treatment. In some embodiments, at least one symptom or defect in a tissue can be decreased, reduced or alleviated by 100% (defect-free or the defect is undetectable by one of skill in the art), as compared to no treatment. In other embodiments, the tissue can be augmented to prevent or delay the onset of defect manifestation in a tissue, e.g., loss of elasticity, firmness, shape and/or volume in a tissue, or signs of wrinkles. As used herein, the phrase "soft tissue augmentation" is generally used in reference to altering a soft tissue structure, including but not limited to, increasing, filling in, restoring, enhancing or replacing a tissue, e.g., to improve the cosmetic or aesthetic appearance of the soft tissue. For example, breast augmentation (also known as breast enlargement, mammoplasty enlargement, augmentation mammoplasty) alters the size and shape of a woman's breasts to improve the cosmetic or aesthetic appearance of the woman. Examples of soft tissue augmentation includes, but is not limited to, dermal tissue augmentation; filling of lines, folds, wrinkles, minor facial depressions, and cleft lips, especially in the face and neck; correction of minor deformities due to aging or disease, including in the hands and feet, fingers and toes; augmentation of the vocal cords or glottis to rehabilitate speech, dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; bulking agent for periurethral support, filling of indentations in the soft tissue, dermal or subcutaneous, due to, e.g., overzealous liposuction or other trauma; filling of acne or traumatic scars; filling of nasolabial lines, nasogiabellar lines and intraoral lines. In some embodiments, the injectable compositions and/or silk fibroin matrices described herein can be used to treat facial lipodystrophies. In some embodiments, the injectable compositions can be used for breast augmentation and/or reconstruction.

In some embodiments, the injectable compositions can be used for soft tissue repair. The term "repair" or "repairing" as used herein, with respect to a tissue, refers to any correction, reinforcement, reconditioning, remedy, regenerating, filling of a tissue that restores volume, shape and/or function of the tissue. In some embodiments "repair" includes full repair and partial repair. For example, the volume, shape and/or function of a tissue to be repaired can be restored by at least about 30%, at least about 40%, at least about 50%, at least about 60%, at least about 70%, at least about 80% or higher, as compared to no treatment. In some embodiments, the volume, shape and/or function of a tissue to be repaired can be restored by at least about 90%, at least about 95%, at least about 97%, or higher, as compared to no treatment. In some embodiments, the volume, shape and/or function of a tissue to be repaired can be restored by 100% (defect-free or the defect is undetectable by one of skill in the art), as compared to no treatment. In various embodiments, the injectable compositions can be used to repair any soft tissues discussed earlier, e.g., breast, skin, and any soft tissues amenable for soft tissue augmentation. In some embodiments, the term "repair" or "repairing" are used herein interchangeably with the term "regeneration" or "regenerate" when used in reference to tissue treatment.

In some embodiments, the injectable compositions can be used for soft tissue reconstruction. As used herein, the phrase "soft tissue reconstruction" refers to rebuilding a soft tissue structure that was severely damaged or lost, e.g., by a dramatic accident or surgical removal. For example, breast reconstruction is the rebuilding of a breast, usually in women. Conventional methods of construct a natural-looking breast generally involve using autologous tissue or prosthetic material. In some embodiments, such breast reconstruction can include reformation of a natural-looking areola and nipple, wherein such procedure can involve the use of implants or relocated flaps of the patient's own tissue. In some embodiments, administration of injectable compositions and/or silk fibroin matrices into a soft tissue region to be reconstructed can maintain the shape and/or size of the reconstructed soft tissue structure for a period of time, e.g., at least 6 weeks, at least about 2 months, at least about 3 months or longer.

Without wishing to be bound, some embodiments of the injectable compositions can be used for hard tissue (e.g., musculoskeletal) augmentation or repair, such as augmentation or repair of bone, cartilage and ligament.

The injectable compositions and silk fibroin matrix described herein can also be used for filling a tissue located at or near a prosthetic implant, for example, but not limited to, a conventional breast implant or knee replacement implant. In some embodiments, the injectable compositions and silk fibroin matrices can be used to interface between a prosthetic implant and a tissue, e.g., to fill a void between the prosthetic implant and the tissue, and/or to prevent the tissue in direct contact with the prosthetic implant. By way of example only, after placing a prosthetic implant (e.g., a breast implant) in a subject, an injectable composition described herein can be introduced at or adjacent to the implant to fill any void between the implant and the tissue (e.g., breast tissue) and/or "sculpt" the tissue for a more natural look.

In any of the uses described herein, silk fibroin matrix can be combined with cells for purposes of a biologically enhanced repair. Cells could be collected from a multitude of hosts including but not limited to human autograft tissues, or transgenic mammals. More specifically, human cells used can comprise cells selected from stem cells (e.g., adipocyte-derived stem cells), osteocytes, fibroblasts, lipocytes, assorted immunocytes, cells from lipoaspirate or any combinations thereof. In some embodiments, the cells can be added after rinsing of the silk fibroin matrices themselves. They can be blended into the silk fibroin matrices, carrier solution, or mixture of silk fibroin matrices and carrier solution prior to injection.

In some embodiments, administering the cells (e.g., stem cells or lipoaspirate) with silk fibroin matrices or an injectable composition described herein can enhance or accelerate host integration and/or tissue formation over time. The cells can be mixed with the silk fibroin matrix or an injectable composition described herein, or they can be administered prior to, concurrently with, or after the silk fibroin matrix or an injectable composition is introduced into a target site. Without wishing to be bound by theory, the cells can secrete pro-angiogenic factors and/or growth factors at the target site. As the tissue regenerates or remodels to fill up a void or repair a defect, the silk fibroin matrix can degrade accordingly. In some embodiments, the silk fibroin matrix can integrate with the regenerated host tissue.

In addition, active agents such as therapeutic agents, pharmaceuticals, or specific growth factors added to the silk fibroin matrices for purposes of improved outcome can be introduced at any or a combination of several points throughout the silk fibroin matrix production process. In some embodiments, these factors can be added to silk fibroin solution or the accelerant phase prior to drying and solidification, they can be soaked into the silk fibroin matrix during the accelerant rinsing process, or they can be coated onto the bulk silk fibroin following rinsing. In some embodiments, smaller silk fibroin matrices used for tissue repair or augmentation can be cut out from a larger silk fibroin matrix, before introducing an active agent into the smaller silk fibroin matrices. For example, an active agent can be soaked into the silk fibroin matrices, coated onto the silk fibroin matrices, or introduced into a carrier fluid before or after blending with the silk fibroin matrices.

In some aspects, the injectable composition and silk fibroin matrices described herein can be used as tissue space fillers. In one embodiment, the tissue space filler is a dermal filler. The dermal filler can be used to improve skin appearance or condition, including, but not limited to, rehydrating the skin, providing increased elasticity to the skin, reducing skin roughness, making the skin tauter, reducing or eliminating stretch lines or marks, giving the skin better tone, shine, brightness, and/or radiance, reducing or eliminating wrinkles in the skin, providing wrinkle resistance to the skin and replacing loss of soft tissue.

A dermal filler comprising a silk fibroin matrix can be modulated for its hardness and opacity through alteration of silk fibroin concentration and formulation method. In one embodiment, a dermal filler can be produced by forming a silk fibroin matrix (or foam), e.g., from a silk fibroin solution of about 1% (w/v) to about 6% (w/v) such that they can be compressed and injected into a tissue through a needle or cannula. The needle or cannula can have an outer diameter of no larger than 4 mm, no larger than 3 mm, no larger than 2 mm, no larger than 1 mm, no larger than 0.8 mm, no larger than 0.6 mm, no larger than 0.4 mm, no larger than 0.2 mm or no larger than 0.1 mm. In some embodiments, the needle or cannula gauge can range from 10 to 34, 11 to 34, 12 to 32, or 13 to 30. In some embodiments, the size of the needle or cannula can be determined to allow for an appropriate extrusion force of at least 40N. Depending on the size of the silk fibroin matrix to be injected. In some embodiments, the size of the needle or cannula can be determined to allow for an appropriate extrusion force of less than 40 N (nominal deliverable injection force for a human hand).

Accordingly, another aspect provided herein relates to a method of improving a condition and/or appearance of skin in a subject in need thereof. Non-limiting examples of a skin condition or and/or appearance include dehydration, lack of skin elasticity, roughness, lack of skin tautness, skin stretch line and/or marks, skin paleness, and skin wrinkles. The method comprises injecting an injectable composition described herein into a dermal region of the subject, wherein the injection improves the skin condition and/or appearance. For example, improving a skin appearance include, but are not limited to, rehydrating the skin, providing increased elasticity to the skin, reducing skin roughness, making the skin tauter, reducing or eliminating stretch lines or marks, giving the skin better tone, shine, brightness and/or radiance to reduce paleness, reducing or eliminating wrinkles in the skin, and providing wrinkle resistance to the skin.

As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis include, but are not limited to, keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Stretch marks from pregnancy are also located in the dermis.

The hypodermis is not part of the skin, and lies below the dermis. Its purpose is to attach the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In one embodiment, provided herein is a method of treating skin dehydration, which comprises injecting to a dermal region suffering from skin dehydration an injectable composition described herein, e.g., wherein the composition comprises a silk fibroin matrix, and optionally a carrier and/or an active agent, and wherein the injection of the composition rehydrates the skin, thereby treating skin dehydration.

In another embodiment, a method of treating a lack of skin elasticity comprises injecting to a dermal region suffering from a lack of skin elasticity an injectable composition described herein, e.g., wherein the composition comprises a plurality of a silk fibroin matrix, and optionally a carrier and/or an active agent, and wherein the injection of the composition increases the elasticity of the skin, thereby treating a lack of skin elasticity.

In yet another embodiment, a method of treating skin roughness comprises injecting to a dermal region suffering from skin roughness an injectable composition described herein, e.g., wherein the composition comprises a silk fibroin matrix, and optionally a carrier and/or an active agent, and wherein the injection of the composition decreases skin roughness, thereby treating skin roughness.

In still another embodiment, a method of treating a lack of skin tautness comprises injecting to a dermal region suffering from a lack of skin tautness an injectable composition described herein, e.g., wherein the composition comprises a silk fibroin matrix as described herein, and optionally a carrier and/or an active agent, and wherein the injection of the composition makes the skin tauter, thereby treating a lack of skin tautness.

In a further embodiment, a method of treating a skin stretch line or mark comprises injecting to a dermal region suffering from a skin stretch line or mark an injectable composition described herein, e.g., wherein the composition comprises a silk fibroin matrix as described herein, and optionally a carrier and/or an active agent, and wherein the injection of the composition reduces or eliminates the skin stretch line or mark, thereby treating a skin stretch line or mark.

In another embodiment, a method of treating skin wrinkles comprises injecting to a dermal region suffering from skin wrinkles an injectable composition described herein, e.g., wherein the composition comprises a silk fibroin matrix, and optionally a carrier and/or an active agent, and wherein the injection of the composition reduces or eliminates skin wrinkles, thereby treating skin wrinkles.

In yet another embodiment, a method of treating, preventing or delaying the formation of skin wrinkles comprises injecting to a dermal region susceptible to, or showing signs of wrinkles an injectable composition described herein, e.g., wherein the composition comprises a silk fibroin matrix, and optionally a carrier and/or an active agent, and wherein the injection of the composition makes the skin resistant to skin wrinkles, thereby treating, preventing or delaying the formation of skin wrinkles.

The effective amount/size and administration schedule of silk fibroin matrices injected into a dermal region can be determined by a person of ordinary skill in the art taking into account various factors, including, without limitation, the type of skin condition, the location of the skin condition, the cause of the skin condition, the severity of the skin condition, the degree of relief desired, the duration of relief desired, the particular silk fibroin matrix formulation used, the rate of degradation or volume retention of the particular silk fibroin matrix formulation used, the pharmacodynamics of the particular silk fibroin matrix formulation used, the nature of the other compounds included in the particular silk fibroin matrix formulation used, the particular characteristics, history and risk factors of the individual, such as, e.g., age, weight, general health, and any combinations thereof. In some embodiments, the silk fibroin matrix can be injected into a dermal region every 3 months, every 6 months, every 9 months, every year, every two years or longer.

In another aspect, the injectable compositions can be used as a dermal filler for dermal bulking to reconstruct or augment a soft tissue body part, such as, e.g., a lip, a breast, a breast part such as the nipple, a muscle, or any other soft body part where adipose and/or connective tissue is used to provide shape, insulation, or other biological function. In fillers used for these applications, the silk fibroin concentration and/or the amount of a carrier (e.g., saline) added to silk fibroin matrix mixture can be adjusted for the relevant constraints of a given biological environment. For example, silk fibroin matrix for breast augmentation can be adapted for matrix hardness and volume retention through alteration of silk fibroin concentration and processing method. For example, about 1% (w/v) to about 10% (w/v) silk fibroin concentration, optionally containing an active agent, e.g., adipose cells such adipose-derived stem cells or cells from lipoaspirate, can be used to produce the silk fibroin matrix. Carrier content in the case of saline can be on the order of 0% to 25% (v/v). Other factors such as, e.g., defect type, defect size and needs for a specific depth of injection of the filler, should be also considered.

Without wishing to be bound, while injection is minimally-invasive, other administration method can be also be used, e.g., implantation, when needed, e.g., to repair or argument a large defect area. For example, for dermal injection and lip augmentation, a syringe needle sized 26 g-30 g can be used. In applications involving large quantities of filler, e.g., breast reconstruction or augmentation, a larger matrix size and a larger bore needle or smaller needle gauge such as 23 g-27 g can be used to administer the filler. In some embodiments, surgery, e.g., implantation, can also be employed to administer large quantities of filler and/or to reach a certain depth of tissues.

Accordingly, in a further aspect, provided herein relates to a method of soft tissue reconstruction, repair, or augmentation, the method comprising administering an injectable composition described herein to a soft tissue region of an individual in need thereof; wherein the composition comprises a silk fibroin matrix as described herein, and optionally an active agent and/or a carrier. Administration methods of an injectable composition described herein can be determined by an ordinary artisan. In some embodiments, the administration method can be injection. In some embodiments, the administration method can be surgery, e.g., implantation.

While injectable compositions and/or silk fibroin matrices described herein can be directly applied on a target region (e.g., injection or surgery). In some embodiments, an injectable composition and/or silk fibroin matrix disclosed herein can also be used to fill an expandable implantable medical device, such as, e.g., an expandable breast implant shell, which is placed in a defect area. In such embodiments, provided herein is a method of soft tissue reconstruction, repair or augmentation, the method comprising placing an implantable medical device into a soft tissue region of an individual at the desired location; and expanding the device by filling the device with silk fibroin matrix and/or injectable compositions described herein, wherein expansion of the medical device by filling it with silk fibroin matrix and/or injectable compositions described herein can reconstruct or augment the soft tissue.

The silk fibroin matrices or injectable compositions disclosed herein can be also used in conjunction with interventional radiology embolization procedures for blocking abnormal blood (artery) vessels (e.g., for the purpose of stopping bleeding) or organs (to stop the extra function e.g., embolization of the spleen for hypersplenism) including uterine artery embolization for percutaneous treatment of uterine fibroids. Modulation of silk fibroin matrix hardness and volume retention rate can be done through alteration of silk fibroin concentration and processing methods as described earlier.

The silk fibroin matrices or injectable compositions disclosed herein can be used to repair void space in a spine, e.g., created by spine disk nucleus removal surgery, to help maintain the normal distance between the adjacent vertebral bodies. In some embodiments, a vertebral disc filler comprising a plurality of silk fibroin matrices can be used to repair void space present in the spine, e.g., between vertebral bodies, and/or in a ruptured spine disk. In such embodiments, a silk fibroin concentration of about 1% (w/v) to about 10% (w/v) can be used to fabricate the silk fibroin matrix described herein. Accelerant and/or active agents can also be mixed with silk fibroin matrix and/or injectable compositions before, during, or after injection into the site of interest.

The silk fibroin matrix or injectable compositions disclosed herein can be used to fill up the vitreous cavity to support the eyeball structure and maintain the retina's position. The viscosity of the injectable composition described herein can be adjusted for the viscosity of vitreous fluid in the eye by one of skill in the art.

In some embodiments, the silk fibroin matrix and/or injectable compositions can be used as a template for tissue reconstruction or augmentation, e.g., soft tissue reconstruction or augmentation (e.g., breast augmentation), or even for small bone or cartilage defects such as fractures. The administration of silk fibroin matrices or injectable compositions described herein can be used to facilitate cartilage/bone cell ingrowth and proliferation and support collagen matrix deposition thus to improve cartilage/bone repair. In another aspect, prior to administration, donor cartilage cells can be seeded or mixed with silk fibroin matrices and/or injectable compositions described herein to expand cell population and thus to promote the development of cartilage tissue. In some embodiments, specific growth factors such as TGF-β or bone morphogenic proteins (BMPs) which support cartilage or bone tissue formation, respectively, can be added into silk fibroin matrices.

In another embodiment, the silk fibroin matrices and/or injectable compositions described herein can be used for facial plastic surgery, such as, e.g., nose reconstruction. The reconstruction strategy discussed above for repairing a cartilage/bone defect can also be applicable for facial plastic surgery.

In some embodiments, the silk fibroin matrices and/or injectable compositions described herein can be used as scaffolds to support cell growth for tissue engineering. For example, the silk fibroin matrices and/or injectable compositions described herein can be administered into an incision or wound site to promote wound healing or wound disclosure. The methods generally comprise administering an injectable composition or silk fibroin matrices described herein, at the wound or incision site and allowing the wound or incision to heal while the silk fibroin matrix is eroded or absorbed in the body and is replaced with the individual's own viable tissue. The methods can further comprise seeding the silk fibroin matrices or mixing the injectable composition with viable cellular material, either from the individual or from a donor, prior to or during administration.

In another aspect, the injectable composition comprising a silk fibroin matrix can be used, directly or indirectly, in methods of repairing, augmenting, or reconstructing a tissue in a subject, e.g., augmenting or reconstructing the breast of a human being. In some embodiments, the injectable compositions or a silk fibroin matrix can be directly placed into a tissue (e.g., a breast tissue) to be repaired or augmented, e.g., by injection. The injectable compositions or a silk fibroin matrix can be injected into a tissue (e.g., a breast tissue) every 6 months, every year, every 2 years, every 3 years, or longer. In other embodiments, the injectable compositions or a silk fibroin matrix can be used to enhance support of a conventional tissue implant, e.g., by enhancing support of the lower pole position of a breast implant. In alternative embodiments, the method can generally comprise administering an injectable composition and/or a silk fibroin matrix near or in proximity to a tissue implant, for example, a conventional breast implant, and seeding the injectable composition and/or fibroin matrix with viable cellular material prior to or during administration. In yet another embodiment, an injectable composition and/or a silk fibroin matrix can be used to partially or completely cover a tissue implant (e.g., a breast implant) to provide a beneficial interface with host tissue and to reduce the potential for malpositioning or capsular contracture.

In some embodiments, the silk fibroin matrix and/or injectable compositions described herein can be used as fillers to promote or support adipogenesis, e.g., to treat facial lipodystrophies. In such embodiments, the injectable compositions and/or silk fibroin matrices can be seeded or mixed with adipose-associated cells, such adipose-derived stem cells or lipoaspirate, prior to or concurrently with the injection to a target area suffering from facial lipodystrophies in a subject. In some embodiments, the silk fibroin matrix can be injected every 3 months, every 6 months, every 9 months, every year, or every two years or longer, to maintain the treatment.

In still another embodiment, the silk fibroin matrices and/or injectable compositions described herein can be used as the scaffold for cells useful for peripheral nerve repair. Silk fibroin matrices can be delivered (e.g., via injection) to the location of the nerve defect with or without additional device to aid the connection to the nerve ends. For such purpose, specific growth factors such as nerve growth factor (NGF), which supports nerve regeneration can be added into injectable compositions and/or mixed with silk fibroin matrices prior to or during administration. In such embodiments, softer silk fibroin matrices, e.g., using a silk fibroin concentration of about 0.5 (w/v) to about 3% (w/v), can be used. Depending on the brain microenvironment, harder silk fibroin matrices can also be used. The silk fibroin matrices and/or injectable compositions can be infused with or added with appropriate therapeutic factors according to the methods described above.

Any cells described herein can be seeded upon a surface of silk fibroin matrices described herein. For example, silk fibroin matrices can be submersed in an appropriate growth medium for the cells of interest, and then directly exposed to the cells. The cells are allowed to proliferate on the surface and interstices of the silk fibroin matrices. The silk fibroin matrices are then removed from the growth medium, washed if necessary, and administered. Alternatively, the cells can be placed in a suitable buffer or liquid growth medium and drawn through silk fibroin matrices by using vacuum filtration. Cells can also be admixed with silk fibroin solution prior to forming silk fibroin matrices, capturing at least some of the cells within the silk fibroin matrices. In another embodiment, the cells of interest can be dispersed into an appropriate solution (e.g., a growth medium or buffer) and then sprayed onto silk fibroin matrices. For example, electro-spraying involves subjecting a cell-containing solution with an appropriate viscosity and concentration to an electric field sufficient to produce a spray of small charged droplets of solution that contain cells.

In some embodiments, the silk fibroin matrices or injectable compositions comprising at least one active agent can be used as a platform for drug delivery. For example, the silk fibroin matrices can be formed with a pharmaceutical agent either entrained in or bound to the matrices and then administered into the body (e.g., injection, implantation or even oral administration). In some embodiments, an active agent can be mixed with silk fibroin matrices and/or injectable compositions and then administered into the body (e.g., injection, implantation or even oral administration). For extended or sustained release, silk fibroin matrices can manipulated, e.g., to modulate its beta-sheet content, for its volume retention and/or degradation rate. To further control the drug release profile, the pharmaceutically-active drug-containing silk fibroin matrices can be mixed with an additional silk fibroin gel phase acting as a carrier either with or without a viscosity inducing component, a surfactant, and/or an included lubricant fluid like saline. The therapeutic-bound silk fibroin matrices can also be further cross-linked to enhance the stability to extend the release period. In an alternative approach, silk fibroin matrices can be mixed with other polymers, for examples, hyaluronic acid, to prolong the release of certain growth factors or cytokines and to stabilize the functionality. Furthermore, the silk fibroin matrices and/or injectable compositions can also be used for coating coaxial drug delivery systems, e.g., by spraying.

As used herein, the term "sustained release" refers to the release of a pharmaceutically-active drug over a period of about seven days or more. In aspects of this embodiment, a drug delivery platform comprising the silk fibroin matrices and/or injectable compositions releases a pharmaceutically-active drug over a period of, e.g., at least about 7 days after administration, at least about 15 days after administration, at least about 30 days after administration, at least about 45 days after administration, at least about 60 days after administration, at least about 75 days after administration, or at least about 90 days after administration.

As used herein, the term "extended release" refers to the release of a pharmaceutically-active drug over a period of time of less than about seven days. In such embodiments, a drug delivery platform comprising the silk fibroin matrix and/or injectable compositions described herein can release a pharmaceutically-active drug over a period of, e.g., about 1 day after administration, about 2 days after administration, about 3 days after administration, about 4 days after administration, about 5 days after administration, or about 6 days after administration.

Depending on the formulation and processing methods of the silk fibroin matrices and the associated applications, the injectable compositions or silk fibroin matrices can be administered (e.g., by injection) periodically, for example, every 3 months, every 4 months, every 5 months, every 6 months, every 7 months, every 8 months, every 9 months, every 10 months, every 11 months, every year, every 2 years or longer. In some embodiments, the injectable compositions or silk fibroin matrices can be administered once to a tissue to be repaired or augmented, and the tissue can regenerate over time to replace the silk fibroin matrices.

In some embodiments of any of the applications described herein, the injectable compositions or silk fibroin matrices can be at least partially dry when administered in a tissue to be repaired or augmented. In some embodiments, the injectable compositions or silk fibroin matrices can be dried (e.g., in the absence of a carrier) when administered in a tissue to be repaired or augmented.

In some embodiments of any of the applications described herein, the injectable compositions or silk fibroin matrices can be at least partially hydrated when administered in a tissue to be repaired or augmented. In some embodiments, the injectable compositions or silk fibroin matrices can be hydrated (e.g., in the presence of a carrier, e.g., a buffered solution and/or lipoaspirate) when administered in a tissue to be repaired or augmented.

In some embodiments of any of the applications described herein, the injectable compositions or silk fibroin matrices can be injected subcutaneously, submuscularly, or intramuscularly.

In some embodiments, the methods and/or compositions described herein can be used in the dermal region. In some embodiments, the methods and/or compositions described herein can be used in the epidermal layer, dermal layer, hypodermis layer, or any combinations thereof.

Delivery Devices and Kits Comprising Silk Fibroin Matrices

Delivery devices comprising an injectable composition or silk fibroin matrices described herein are also provided herein. Delivery devices can be any conventional delivery device used for injection purposes, e.g., a syringe, or a custom-made delivery device, such as an injection gun. Accordingly, a further aspect provided herein is an injection device comprising an injectable composition or a silk fibroin matrix.

In some embodiments, the delivery device can further comprise a tubular structure for introducing the silk fibroin matrix into a tissue to be repaired or augmented. In some embodiments, the tubular structure can be tapered. For example, the tapered tubular structure can comprise a conical interior space. Examples of the tubular structures can include, without limitations, a needle, a cannula, a catheter, any art-recognized injection applicator, and any combinations thereof.

In some embodiments, the delivery device can further comprise a mechanical element (e.g., an elongated structure such as a ramrod) to facilitate the exit of the compressed silk fibroin matrix through the tubular structure.

In various embodiments, the delivery device can include an injection carrier, e.g., a buffered solution.

In various embodiments, the delivery device (e.g., a syringe) can include an anesthetic.

Further provided herein is a kit comprising one embodiment of an injectable composition or silk fibroin matrix packaged in a delivery applicator, such as a catheter, a needle or a cannula. In some embodiments, a local anesthetic can be blended with the injectable composition or silk fibroin matrix. In alternative embodiments, a local anesthetic can be packaged in a separate container. For example, it is desirable to apply a local anesthetic to a target tissue to be treated prior to further treatment. An exemplary anesthetic includes, but is not limited to, lidocaine. Dependent upon application, the kit can include syringes sizes from 0.5 mL to 60 mL, where applications requiring larger volumes (e.g., bone fillers, disc fillers) are supplied in a larger size syringe. Additionally, needle gauge can adjusted according to injection site with an acceptable range of 10 g to 30 g needles. For example, 10 g to 20 g needles can be used for intradermal injections.

In some embodiments, the kit can further comprise a plurality of delivery devices preloaded with an injectable composition or silk fibroin matrices described herein. Each delivery device can be individually packaged.

In some embodiments, the kit can further comprise a container containing a buffered solution or an injection carrier.

In some embodiments, the kit can further comprise at least one additional empty syringe. In some embodiments, the kit can further comprise at least one additional needle. In some embodiments, the kit can further comprise at least one catheter or cannula.

Embodiments of the various aspects described herein can be illustrated by the following numbered paragraphs.

1. A method for repairing or augmenting a tissue in a subject comprising: placing into the tissue to be repaired or augmented a composition comprising a compressed silk fibroin matrix, wherein the compressed silk fibroin matrix expands upon placement into the tissue, and retains at least about 1% of its original expanded volume within the tissue for at least about 2 weeks.
2. The method of paragraph 1, wherein the compressed silk fibroin matrix expands in volume by at least about 2-fold, relative to the volume of the compressed silk fibroin matrix.
3. The method of paragraph 1 or 2, wherein the silk fibroin matrix retains at least about 50% of its original expanded volume within the tissue for at least about 2 weeks, at least about 6 weeks, or at least about 3 months.
4. The method of any of paragraphs 1-3, wherein the silk fibroin matrix retains at least about 50% of its original expanded volume within the tissue for at least about 6 months.
5. The method of any of paragraphs 1-4, wherein the silk fibroin matrix retains at least about 60% of its original expanded volume within the tissue for at least about 6 weeks.
6. The method of paragraph 5, wherein the silk fibroin matrix retains at least about 70% of its original expanded volume within the tissue for at least about 6 weeks.
7. The method of paragraph 6, wherein the silk fibroin matrix retains at least about 80% of its original expanded volume within the tissue for at least about 6 weeks.
8. The method of any of paragraphs 1-7, wherein the silk fibroin matrix retains at least about 70% of its original expanded volume within the tissue for at least 3 months.
9. The method of any of paragraphs 1-8, wherein the silk fibroin matrix is adapted to degrade no more than 50% of its original expanded volume in at least about 6 weeks.
10. The method of paragraph 9, wherein the silk fibroin matrix is adapted to degrade no more than 50% of its original expanded volume in at least about 3 months.
11. The method of any of paragraphs 1-10, wherein the silk fibroin matrix is adapted to degrade no more than 30% of its original expanded volume in at least about 6 weeks.
12. The method of paragraph 11, wherein the silk fibroin matrix is adapted to degrade no more than 10% of its original expanded volume in at least about 6 weeks.
13. The method of any of paragraphs 1-12, wherein the silk fibroin matrix is adapted to degrade no more than 30% of its original expanded volume in at least about 3 months.
14. The method of any of paragraphs 1-13, wherein the silk fibroin matrix is porous.

15. The method of paragraph 14, wherein the porous silk fibroin matrix has a porosity of at least about 1%, at least about 5%, at least about 10%, at least about 15%, or at least about 30%.
16. The method of paragraph 15, wherein the porous silk fibroin matrix has a porosity of at least about 50%.
17. The method of paragraph 16, wherein the porous silk fibroin matrix has a porosity of at least about 70%.
18. The method of any of paragraphs 14-17, wherein the pores have a size of about 1 µm to about 1500 µm.
19. The method of paragraph 18, wherein the pores have a size of about 50 µm to about 650 µm.
20. The method of any of paragraphs 1-19, wherein the silk fibroin matrix is formed from a silk fibroin solution of about 0.1% w/v to about 30% w/v.
21. The method of paragraph 20, wherein the silk fibroin solution of about 0.5% w/v to about 10% w/v.
22. The method of paragraph 21, wherein the silk fibroin solution is about 1% w/v to about 6% w/v.
23. The method of any of paragraphs 1-22, wherein the fibroin matrix is freezer-processed.
24. The method of any of paragraphs 1-23, wherein the silk fibroin matrix is a silk fibroin foam.
25. The method of any of paragraphs 1-24, wherein the composition or the silk fibroin matrix further comprises at least one active agent.
26. The method of paragraph 25, wherein the at least one active agent is a biologically active agent, a cosmetically active agent, a cell attachment agent, or any combinations thereof.
27. The method of paragraph 26, wherein the biologically active agent is selected from the group consisting of a therapeutic agent, an anesthetic, a cell growth factor, a peptide, a peptidomimetic, an antibody or a portion thereof, an antibody-like molecule, nucleic acid, a polysaccharide, and any combinations thereof.
28. The method of paragraph 26, wherein the cell attachment agent is selected from the group consisting of hyaluronic acid, collagen, crosslinked hyaluronic acid/collagen, an integrin-binding molecule, chitosan, elastin, fibronectin, vitronectin, laminin, proteoglycans, any derivatives thereof, any peptide or oligosaccharide variants thereof, and any combinations thereof.
29. The method of paragraph 26, wherein the cosmetically active agent is selected from the group consisting of an anti-aging agent, an anti-free radical agent, an antioxidant, a hydrating agent, a whitening agent, a colorant, a depigmenting agent, a sun-blocking agent, a muscle relaxant, and any combinations thereof.
30. The method of any of paragraphs 1-29, wherein the composition further comprises a cell.
31. The method of paragraph 30, wherein the cell is a stem cell.
32. The method of any of paragraphs 1-31, wherein the composition further comprises a biological fluid or concentrate.
33. The method of paragraph 32, wherein the biological fluid or concentrate is lipoaspirate, bone marrow aspirate, or any combinations thereof.
34. The method of any of paragraphs 1-33, wherein the composition or the silk fibroin matrix further comprises a hydrogel.
35. The method of any of paragraphs 1-34, wherein the composition or the silk fibroin matrix further comprises a dermal filler material.
36. The method of paragraph 35, wherein the dermal filler material is selected from the group consisting of poly (methyl methacrylate) microspheres, hydroxylapatite, poly(L-lactic acid), hyaluronic acid, collagen, gelatin, and any combinations thereof.
37. The method of any of paragraphs 1-36, wherein the composition further comprises a carrier.
38. The method of any of paragraphs 1-37, wherein the silk fibroin matrix excludes an amphiphilic peptide.
39. The method of paragraph 38, wherein the amphiphilic peptide comprises a RGD motif.
40. The method of any of paragraphs 1-39, wherein the placement of the compressed silk fibroin matrix is performed by injection.
41. The method of paragraph 40, wherein the injection is performed subcutaneously, submuscularly, or intramuscularly.
42. The method of any of paragraphs 1-41, wherein the tissue is a soft tissue.
43. The method of paragraph 42, wherein the soft tissue is selected from the group consisting of a tendon, a ligament, skin, a breast tissue, a fibrous tissue, a connective tissue, a muscle, and any combinations thereof.
44. The method of paragraph 43, wherein the soft tissue is skin.
45. The method of paragraph 44, wherein the soft tissue is a breast tissue.
46. The method of any of paragraphs 1-45, wherein the subject is a mammalian subject.
47. The method of paragraph 46, wherein the mammalian subject is a human.
48. The method of any of paragraphs 1-47, wherein the silk fibroin matrix is compressed by loading the silk fibroin matrix into an interior space of a delivery applicator, wherein the interior space has a volume smaller than the volume of the silk fibroin matrix in an uncompressed state.
49. The method of paragraph 48, wherein the delivery applicator comprises a needle, a cannula, a catheter, or any combinations thereof.
50. An injectable composition for use in repairing or augmenting a tissue in a subject, comprising a compressed silk fibroin matrix, wherein the compressed silk fibroin matrix expands upon injection into the tissue, and retains at least about 1% of its original expanded volume within the tissue for at least about 2 weeks.
51. The composition of paragraph 50, wherein the compressed silk fibroin matrix expands in volume by at least about 2-fold, relative to the volume of the compressed silk fibroin matrix.
52. The composition of paragraph 50 or 51, wherein the compressed silk fibroin matrix excludes an amphiphilic peptide.
53. The composition of paragraph 52, wherein the amphiphilic peptide comprises a RGD motif.
54. The composition of any of paragraphs 50-53, wherein the silk fibroin matrix retains at least about 50% of its original expanded volume within the tissue for at least about 2 weeks, at least about 6 weeks, or at least about 3 months.
55. The composition of any of paragraphs 50-54, wherein the silk fibroin matrix retains at least about 50% of its original expanded volume within the tissue for at least about 6 months.
56. The composition of any of paragraphs 50-55, wherein the silk fibroin matrix retains at least about 60% of its original expanded volume within the tissue for at least about 6 weeks.

57. The composition of paragraph 56, wherein the silk fibroin matrix retains at least about 70% of its original expanded volume within the tissue for at least about 6 weeks.
58. The composition of paragraph 57, wherein the silk fibroin matrix retains at least about 80% of its original expanded volume within the tissue for at least about 6 weeks.
59. The composition of any of paragraphs 50-58, wherein the silk fibroin matrix retains at least about 70% of its original expanded volume within the tissue for at least 3 months.
60. The composition of any of paragraphs 50-59, wherein the silk fibroin matrix is adapted to degrade no more than 50% of its original expanded volume in at least about 6 weeks.
61. The composition of paragraph 60, wherein the silk fibroin matrix is adapted to degrade no more than 50% of its original expanded volume in at least about 3 months.
62. The composition of any of paragraphs 50-62, wherein the silk fibroin matrix is adapted to degrade no more than 30% of its original expanded volume in at least about 6 weeks.
63. The composition of paragraph 62, wherein the silk fibroin matrix is adapted to degrade no more than 10% of its original expanded volume in at least about 6 weeks.
64. The composition of any of paragraphs 50-63, wherein the silk fibroin matrix is adapted to degrade no more than 30% of its original expanded volume in at least about 3 months.
65. The composition of any of paragraphs 50-64, wherein the silk fibroin matrix is porous.
66. The composition of paragraph 65, wherein the porous silk fibroin matrix has a porosity of at least about 1%, at least about 5%, at least about 10%, at least about 15%, or at least about 30%.
67. The composition of paragraph 66, wherein the porous silk fibroin matrix has a porosity of at least about 50%.
68. The composition of paragraph 67, wherein the porous silk fibroin matrix has a porosity of at least about 70%.
69. The composition of any of paragraphs 65-68, wherein the pores have a size of about 1 µm to about 1500 µm.
70. The composition of paragraph 69, wherein the pores have a size of about 50 µm to about 650 µm.
71. The composition of any of paragraphs 50-70, wherein the silk fibroin matrix is formed from a silk fibroin solution of about 0.1% w/v to about 30% w/v.
72. The composition of paragraph 71, wherein the silk fibroin solution of about 0.5% w/v to about 10% w/v.
73. The composition of paragraph 72, wherein the silk fibroin solution is about 1% w/v to about 6% w/v.
74. The composition of any of paragraphs 50-73, wherein the silk fibroin matrix is freezer-processed.
75. The composition of any of paragraphs 50-74, wherein the silk fibroin matrix is a silk fibroin foam.
76. The composition of any of paragraphs 50-75, wherein the injectable composition or the silk fibroin matrix further comprises at least one active agent.
77. The composition of paragraph 76, wherein the at least one active agent is a biologically active agent, a cosmetically active agent, a cell attachment agent, or any combinations thereof.
78. The composition of paragraph 77, wherein the biologically active agent is selected from the group consisting of a therapeutic agent, an anesthetic, a cell growth factor, a peptide, a peptidomimetic, an antibody or a portion thereof, an antibody-like molecule, nucleic acid, a polysaccharide, and any combinations thereof.
79. The composition of paragraph 77, wherein the cell attachment agent is selected from the group consisting of hyaluronic acid, collagen, crosslinked hyaluronic acid/collagen, an integrin-binding molecule, chitosan, elastin, fibronectin, vitronectin, laminin, proteoglycans, any derivatives thereof, any peptide or oligosaccharide variants thereof, and any combinations thereof.
80. The composition of paragraph 77, wherein the cosmetically active agent is selected from the group consisting of an anti-aging agent, an anti-free radical agent, an anti-oxidant, a hydrating agent, a whitening agent, a colorant, a depigmenting agent, a sun-blocking agent, a muscle relaxant, and any combinations thereof.
81. The composition of any of paragraphs 50-80, further comprising a cell.
82. The composition of paragraph 81, wherein the cell is a stem cell.
83. The composition of any of paragraphs 50-82, further comprising a biological fluid or concentrate.
84. The composition of paragraph 83, wherein the biological fluid or concentrate is lipoaspirate, bone marrow aspirate, or any combinations thereof.
85. The composition of any of paragraphs 50-84, wherein the injectable composition or the silk fibroin matrix further comprises a hydrogel.
86. The composition of any of paragraphs 50-85, wherein the injectable composition or the silk fibroin matrix further comprises a dermal filler material.
87. The composition of paragraph 86, wherein the dermal filler material is selected from the group consisting of poly(methyl methacrylate) microspheres, hydroxylapatite, poly(L-lactic acid), hyaluronic acid, collagen, gelatin and any combinations thereof.
88. The composition of any of paragraphs 50-87, wherein the injectable composition further comprises a carrier.
89. The composition of any of paragraphs 50-88, wherein the compressed silk fibroin matrix has a volume of about 10% to about 90% of its original volume before compression.
90. The composition of any of paragraphs 50-88, wherein the compressed silk fibroin matrix has a volume of no more than 70% of its original volume before compression.
91. A delivery device comprising an injectable composition of any of paragraphs 50-90.
92. The delivery device of paragraph 91, further comprising a tubular structure for introducing the injectable composition into a tissue to be repaired or augmented.
93. The delivery device of paragraph 92, wherein the tubular structure is tapered.
94. The delivery device of paragraph 93, wherein the tapered tubular structure comprises a conical interior space.
95. The delivery device of any of paragraphs 91-94, wherein the tubular structure is a needle, a cannula, a catheter, or any combinations thereof.
96. The delivery device of any of paragraphs 91-95, further comprising a mechanical element to facilitate the exit of the compressed silk fibroin matrix through the tubular structure.
97. The delivery device of any of paragraphs 91-96, further comprising an injection carrier.

Some Selected Definitions of Terms

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. A subject can be male or female. Preferably, the subject is a mammal. The mammal can be a human, non-human primate, mouse, rat, dog, cat, horse, or cow, but are not limited to these examples. Mammals other than humans can be advantageously used as subjects that represent animal models of tissue repair, regeneration and/or reconstruction. In addition, the methods and compositions described herein can be used to treat domesticated animals and/or pets.

The term "statistically significant" or "significantly" refers to statistical significance and generally means a two standard deviation (2SD) below or above a reference level. The term refers to statistical evidence that there is a difference. It is defined as the probability of making a decision to reject the null hypothesis when the null hypothesis is actually true. The decision is often made using the p-value.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell, siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab')2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10); 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (Pluckthun, The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites, (EP 404,097; WO 93/11161; Hollinger et ah, Proc. Natl. Acad. Sd. USA, P0; 6444-6448 (1993)).

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

As used herein, the term "hormones" generally refers to naturally or non-naturally occurring hormones, analogues and mimics thereof. In certain embodiments, the term "hormones" refers to any hormones used in therapeutic treatment, e.g., growth hormone treatment. As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or variant produced by means of recombinant DNA technology, including somatrem, somatotropin, and somatropin. In one embodiment, hormones include insulin.

As used herein, a "contrast agent" can be any chemical moiety that is used to increase the degree of difference between the lightest and darkest part of a scan or an imaging, e.g., during medical scan or imaging, relative to a scan performed without the use of a contrast agent. For example, contrast agents can include imaging agents containing radioisotopes such as indium or technetium; dyes containing iodine, gadolinium or cyanine; enzymes such as horse radish peroxidase, GFP, alkaline phosphatase, or β-galactosidase; fluorescent substances such as europium derivatives; luminescent substances such as N-methylacrydium derivatives or the like. In some embodiments, contrast agents can include gold nanoparticles and/or quantum dots.

As used herein, the term "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

As used herein, the term "comprising" means that other elements can also be present in addition to the defined elements presented. The use of "comprising" indicates inclusion rather than limitation.

The term "consisting of" refers to the components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise explained, all technical and scientific terms used herein have the same meaning as commonly understood by one of ordinary skill in the art to which this disclosure belongs. Definitions of common terms in diseases and disorders, separation and detection techniques can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified throughout the specification are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some embodiments described herein are further illustrated by the following example which should not be construed as limiting.

The contents of all references cited throughout this application, examples, as well as the figures and tables are incorporated herein by reference in their entirety.

EXAMPLES

Example 1. Fabrication of Exemplary Injectable Silk Fibroin-Based Foams

A silk fibroin foam sheet can be produced by any art-recognized methods. In this Example, a silk foam sheet was created by using a freeze-processing technique, for example, freezer-processing of a silk fibroin solution directly.

To prepare a silk fibroin solution, *Bombyx mori* silkworm cocoons purchased from Tajimia Shoji Co. (Yokohama, Japan) or a Taiwanese supplier were cut into pieces, and boiled in 0.02 M $Na_2CO_3$ for about 10-60 minutes, and preferably for about 30 minutes. The resulting silk fibroin fibers were rinsed in distilled water and let dried. The dried silk fibroin fibers were re-solubilized in 9.3 M LiBr at 60° C., for about 1-4 hours, until dissolved. The silk fibroin solution was dialyzed, with a molecular weight cutoff of 3500 Daltons, against distilled water for at least 6 water changes.

Figure 1B:
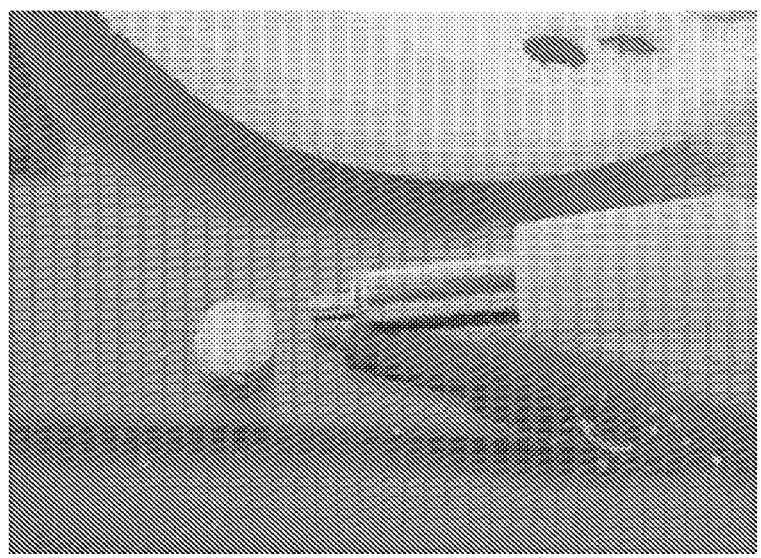

The silk fibroin solution (e.g., with a concentration of about 1% to about 6% w/v), made from Japanese cocoons or Taiwanese cocoons, was poured into a container (e.g., a plastic Petri dish). The silk fibroin solution was then stored and maintained at around 20° F. (~−7° C.) for about 3 days (e.g., stored in an EdgeStar Model FP430 thermoelectric cooler). The resultant silk fibroin material was gel-like, but not a stiff solid. The gel-like silk fibroin material was then freeze-dried for about 3 days (e.g., using a VirTis Genesis (Model 25L Genesis SQ Super XL-70) Lyophilizer). After removal from the lyophilizer, the freeze-dried silk fibroin material became a foam-like material with a very consistent interconnected fine-pore structure. In some embodiments, the silk fibroin foam was further soaked in alcohol (e.g., about 70% methanol) to induce beta sheet formation. In such embodiments, there can be about 10% shrinkage in volume of the silk fibroin foam sheet after treatment with alcohol. The alcohol-treated foam sheet exhibited excellent stiffness and toughness. A 4-mm diameter biopsy punch (FIG. 1A) was then used to cut out small silk fibroin foam disks (approximately 2 mm thickness) from the silk fibroin foam sheet, as shown in FIG. 1B.

Figure 2A:
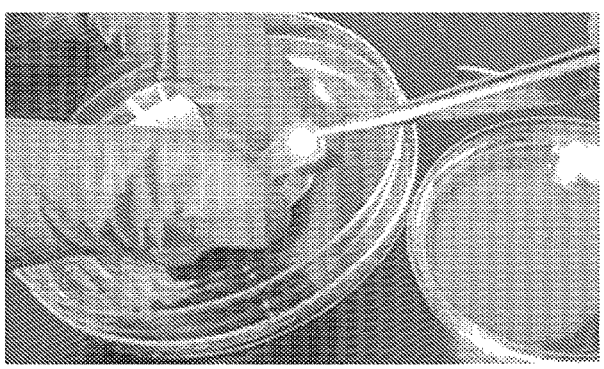
FIGS. 2A-2B show images of an exemplary method of placing a silk fibroin-based injectable foam disk into an injectable position inside an injector tip (e.g., a pipette tip).
Figure 2B:
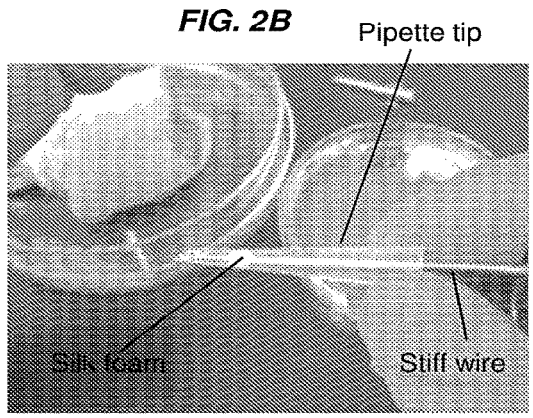
Figure 3A:
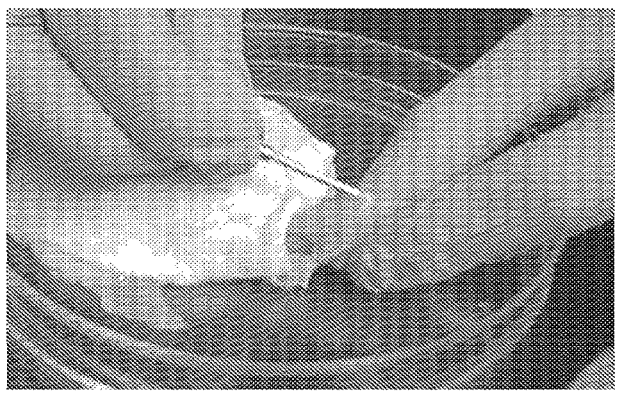
FIGS. 3A-3D show images of an exemplary method of injecting a silk fibroin-based injectable foam disk into a tissue.
Figure 3B:
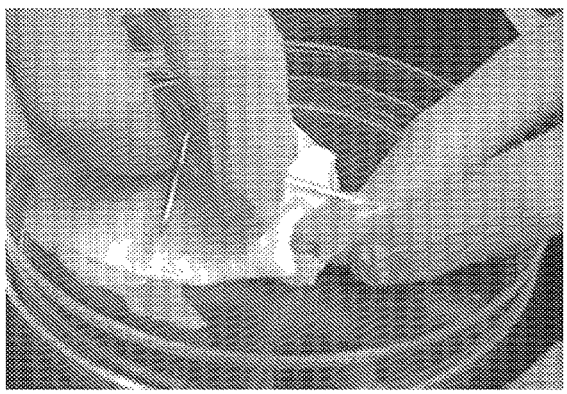
Figure 3C:
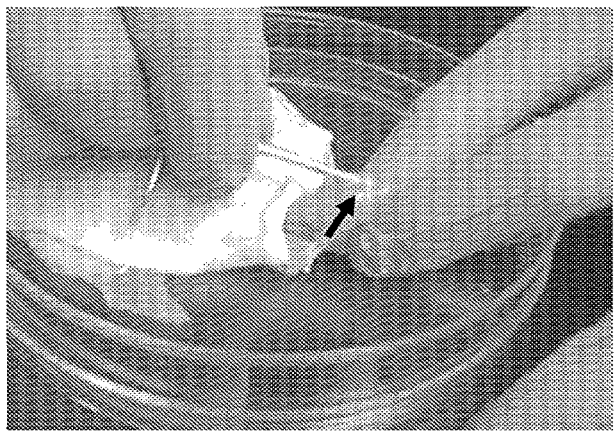
Figure 3D:
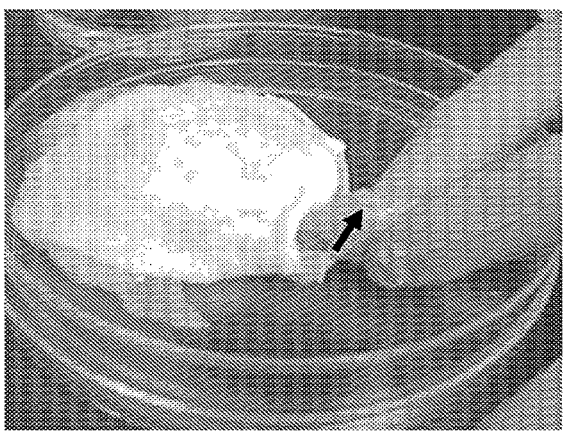

Example 2. Evaluation of the Silk Fibroin-Based Foams for Injection into a Tissue To assess the potential for injecting one or more embodiments of the injectable silk fibroin-based foam constructs into a tissue, an experiment was conducted on raw chicken thighs. FIG. 2A shows a silk fibroin-based foam loaded into a sharpened conical-shaped applicator tip, e.g., a pipette tip. The conical interior space of a pipette tip can allow the foam to be ejected with less friction and force than a straight applicator tip (e.g., a straight needle). The foam was pushed through the pipette tip using a stiff wire (FIG. 2B). By way of example only, in some embodiments, injection of the silk fibroin-based foam into a raw chicken thigh tissue was performed as described below. A straight 14-gauge needle (~1.6 mm inner diameter) was first used to puncture a hole in the meaty part of the chicken thigh (FIG. 3A). The pipette tip loaded with the silk fibroin-based foam was inserted into the hole (FIG. 3B) and slowly drawn out, while the stiff wire was used to eject the foam (FIG. 3C). FIG. 3D shows the foam injected and positioned in the raw chicken thigh. Thus, the silk fibroin-based foams can be injected into a tissue, e.g., for filling a void in the tissue or augmenting the tissue.

Figure 4A:
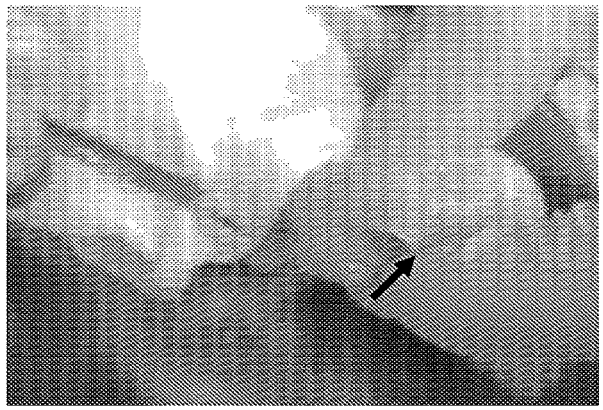
FIGS. 4A-4F show images of an exemplary method of extracting an injected silk fibroin-based foam from a tissue.
Figure 4B:
Figure 4C:
Figure 4D:
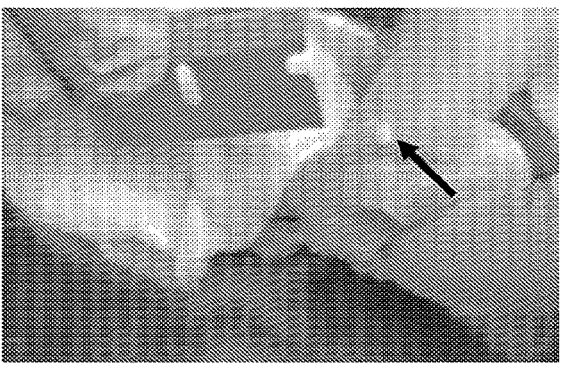
Figure 4E:
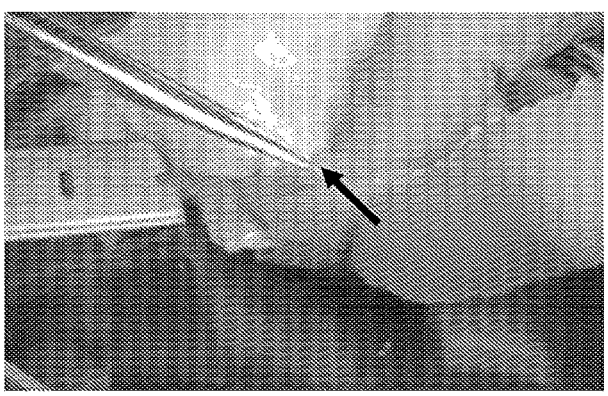
Figure 4F:
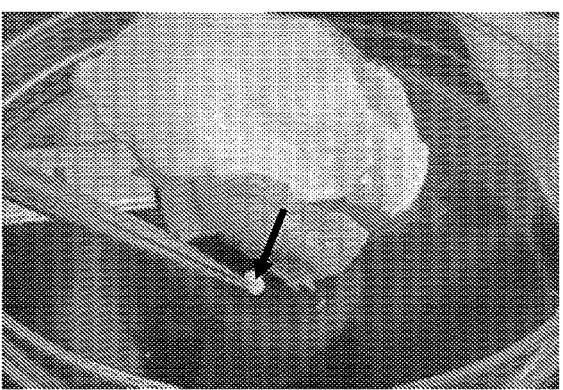

FIGS. 4A-4F show the injected silk fibroin-based foam being excised. For example, a razor blade was used to slice through the raw chicken meat (FIGS. 4A through 4D). Using tweezers, the silk fibroin-based foam was then extracted (FIGS. 4E and 4F). FIG. 4F shows that the extracted silk fibroin-based foam was intact, indicating that the silk fibroin-based foam can remain intact after injection into a tissue.

Example 3. In Vivo Studies of Injectable Silk Fibroin-Based Foams

Figure 5:
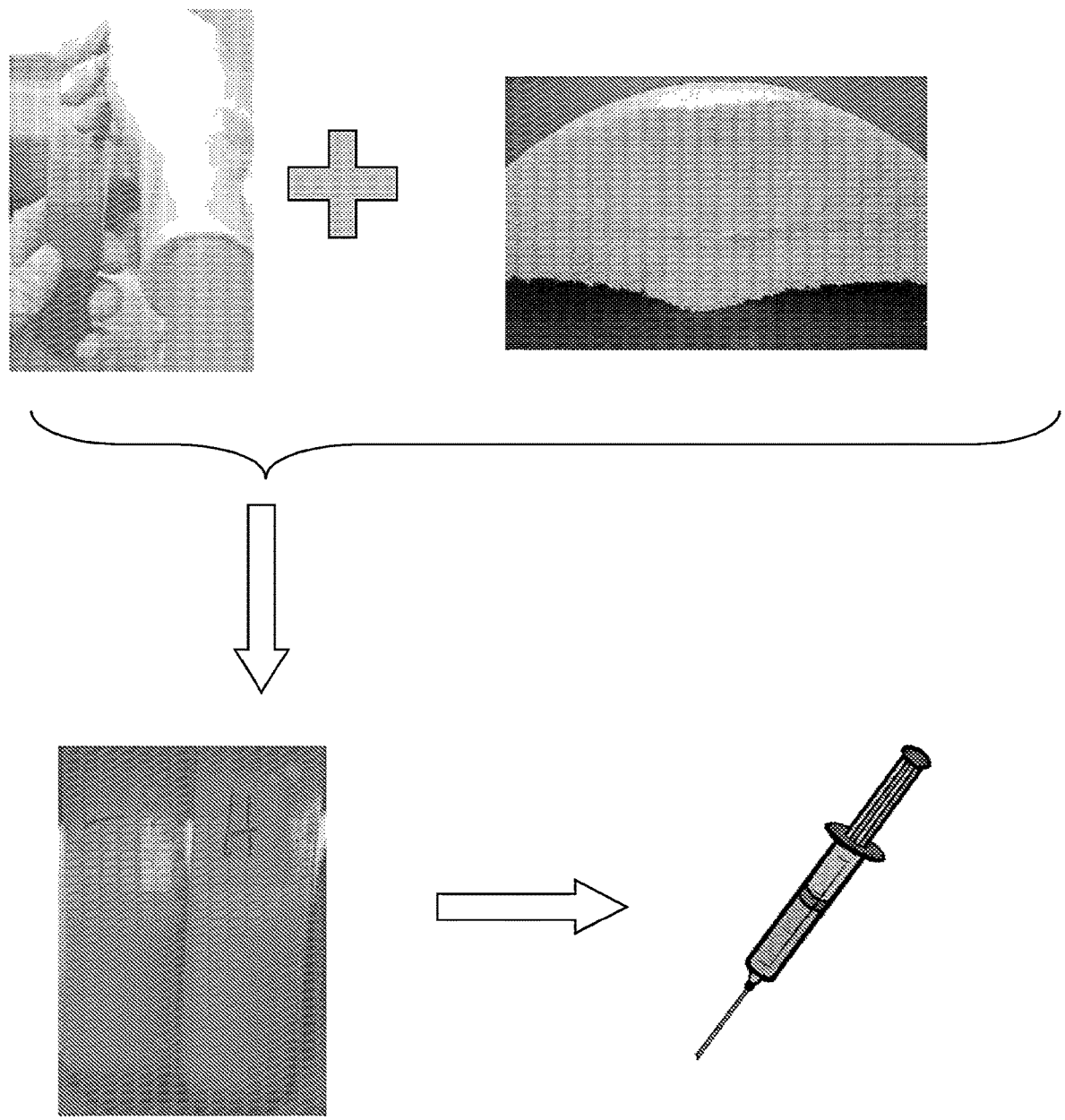
FIG. 5 shows an exemplary method of using one or more embodiments of the injectable compositions described herein. The porous silk fibroin-based foams (e.g., formed by freezer processing) can be mixed with lipoaspirate as a carrier, optionally containing adipose-derived stem cells (ASCs), to form an exemplary injectable composition. The injectable compositions can then be injected into a subject, e.g., an animal model.
Figure 6A:
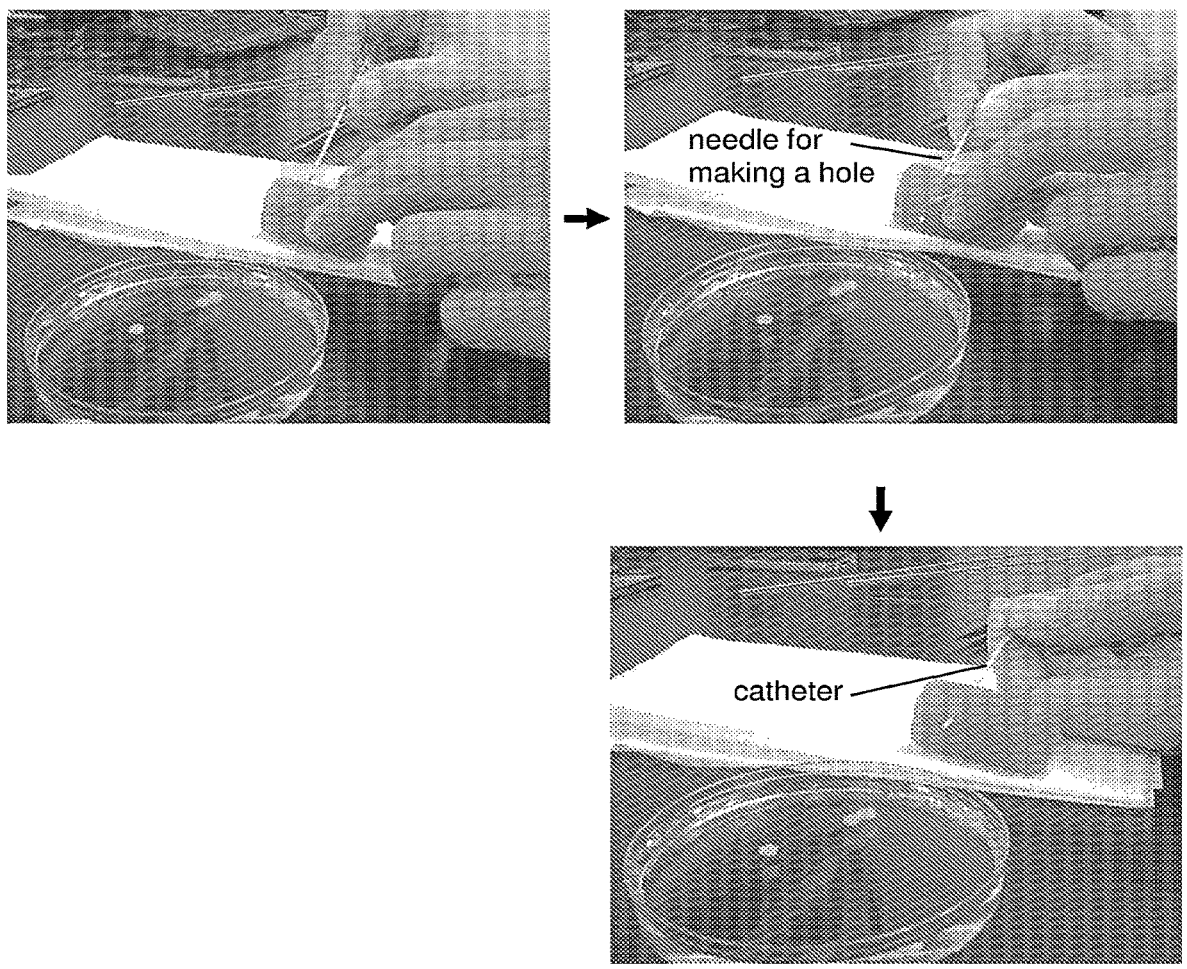
Figure 6C:
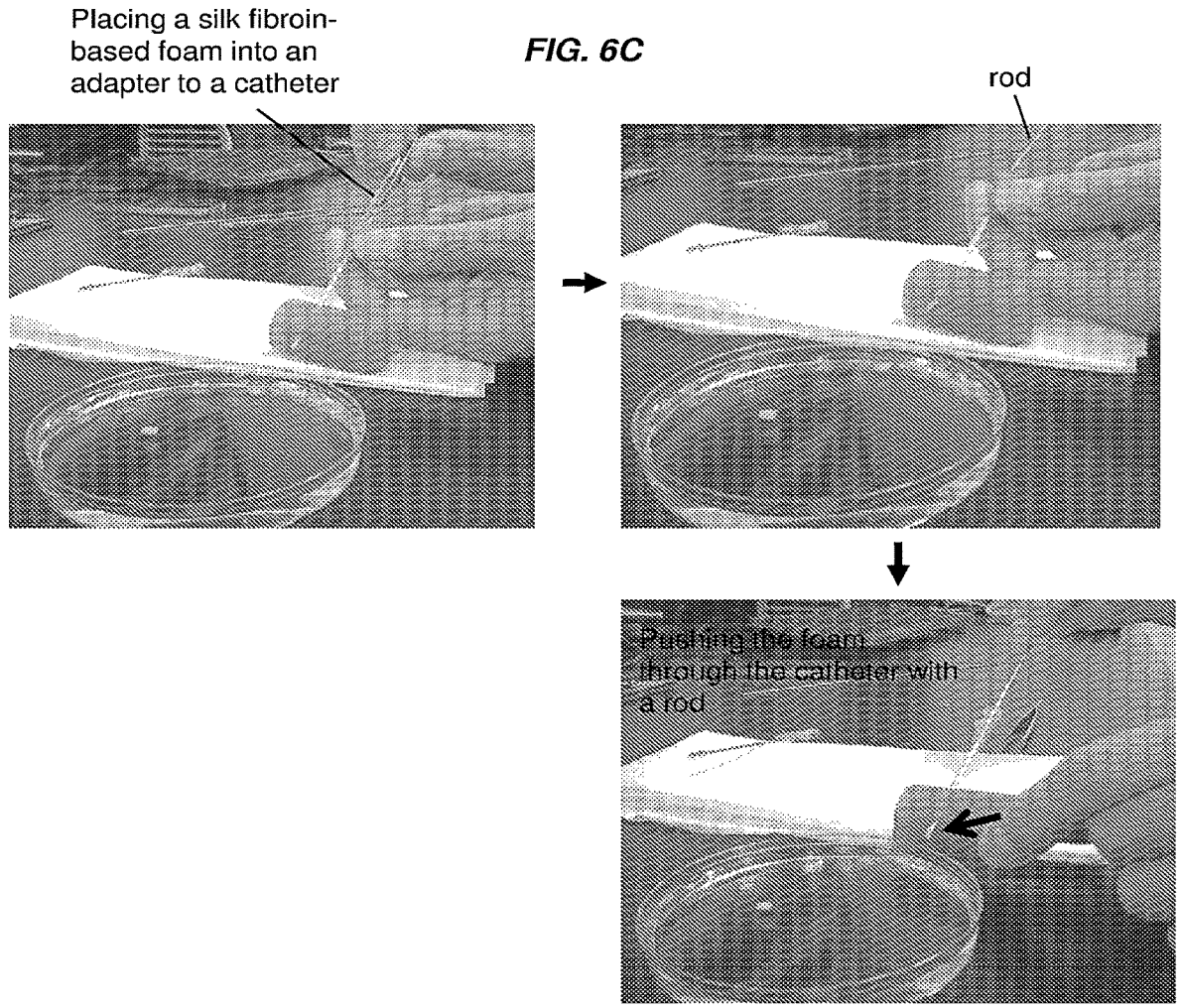

A rat or mouse model was used for assessing some embodiments of the silk fibroin-based foams described herein. Other mammalian models (e.g., rabbit, canine, or porcine models) can also be used depending on the applications of the injectable silk fibroin-based foams and the tissues to be modeled for treatment. The rats or mice were weighed and anesthetized with isoflurane in oxygen prior to injection. A silk fibroin-based foam having a size of about 5 mm in diameter by about 2 mm in height was used for injection. Briefly, dry silk fibroin foams were immersed in saline immediately before loading into a catheter. Alternatively, the dry silk fibroin foam could be immersed in lipoaspirate immediately before loading into a catheter (e.g., as shown in FIG. 5). Subcutaneous injections were performed above the pectoral muscles. Intramuscular and submuscular injections were performed between the pectoralis major and pectoralis minor muscles or underneath the pectoral muscles, respectively. A fanning subcutaneous injection method was performed in the dorsus of the rat or the mouse. Injected samples were explanted, and evaluated for volume retention after 1, 14, 40 and 60 days. Volume retention was performed by 2 methods, e.g., scale measurements and volume displacement.

Figure 7A:
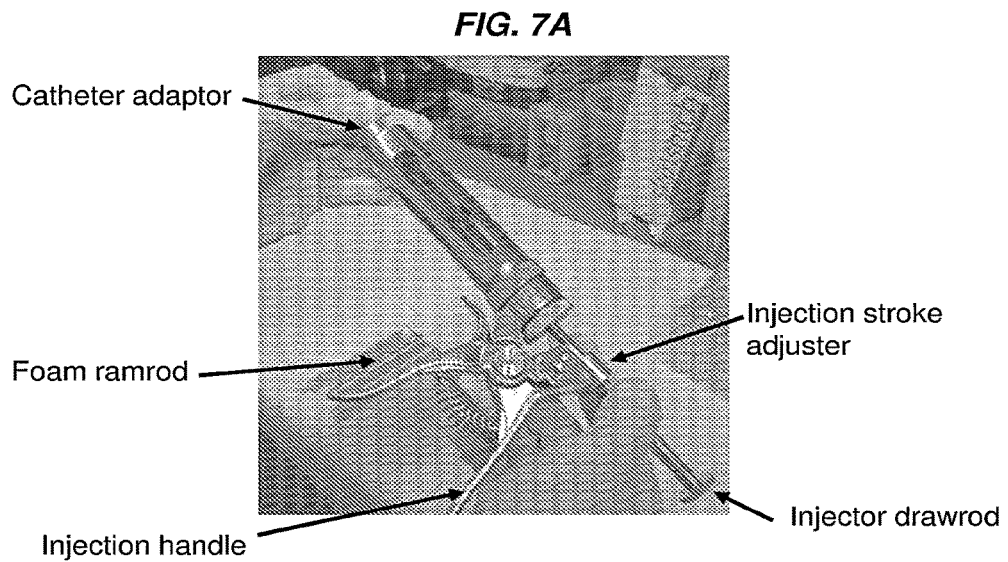
FIGS. 7A-7B show images of an exemplary method of injecting a silk fibroin-based foam into a tissue in vivo.

A rod-and-plunger system can be used to inject a silk fibroin foam into a tissue. For example, FIG. 7A shows an exemplary Hauptner syringe that was custom-modified to inject a silk fibroin foam subcutaneously in vivo, e.g., in a mouse or rat model. The design is, at least in part, based on a commercially available pistol-style (Hauptner) syringe made by Ideal Instruments. This Hauptner syringe device has a spring-loaded handle that generally forces an Injector Drawrod into the syringe body by a pre-set distance (using the injection Stroke Adjuster). To modify the Hauptner syringe device for injecting a foam, rather than a solution or a gel, a Foam Ramrod was manufactured to fit through the end of the syringe, where the Catheter Adaptor is located, as shown in FIG. 7A. A catheter is attached to the adaptor. Typically, a catheter is a tube that is used to remove fluid from the body. In some embodiments, a tapered catheter (i.e., the barrel of the catheter is larger than the catheter tip) can be used to inject a silk fibroin foam into a tissue. The taper allows a foam to be pre-positioned in the barrel before attaching the catheter to the Hauptner syringe and allows the foam to be gradually compressed during the process of injection.

Figure 7B:
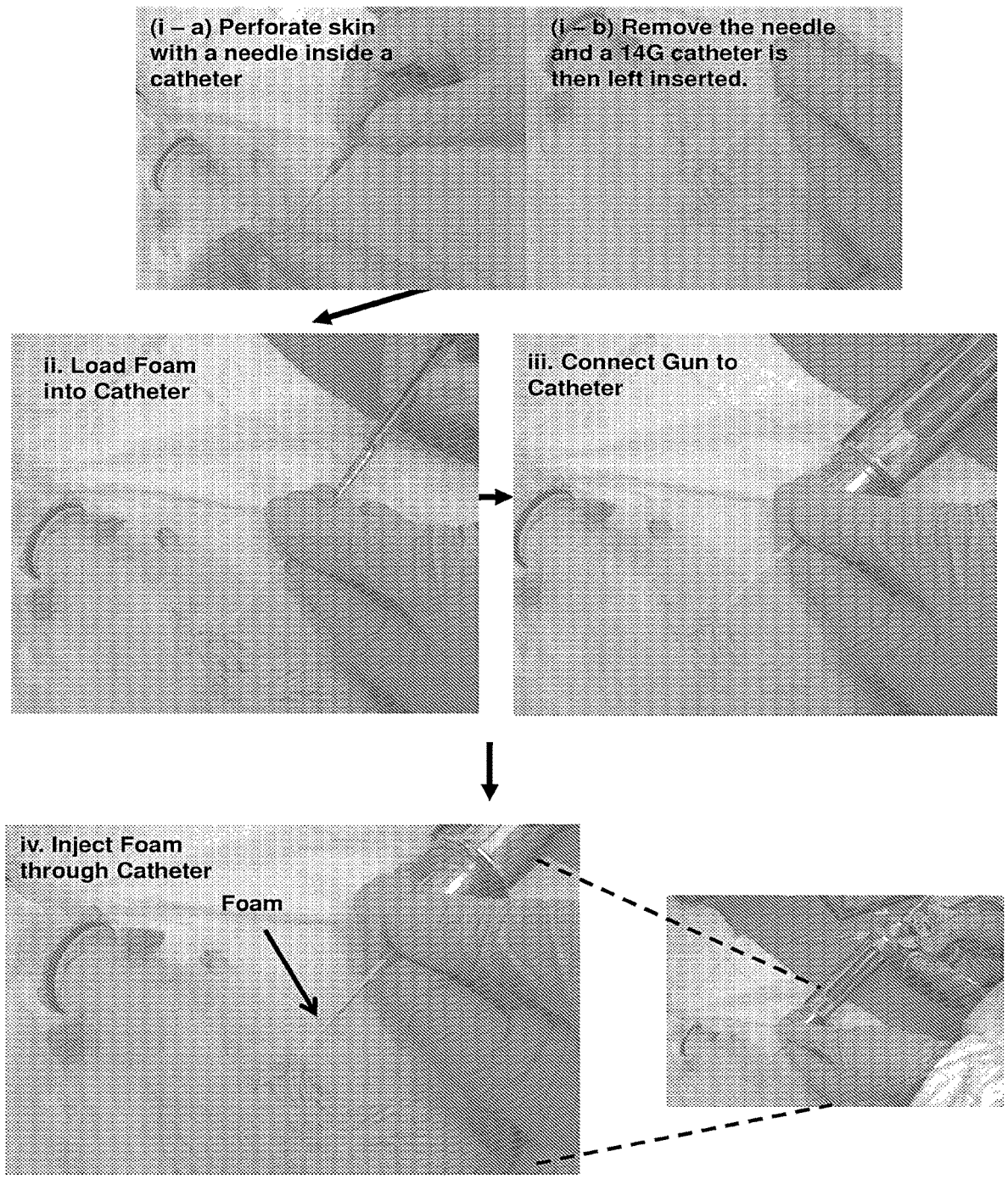

By way of example only, the rat or mouse study protocol involved the initial creation of a small hole in the rat or mouse skin using a 14 gauge needle positioned within the catheter (e.g., as shown in FIG. 7B, step 1: left panel). The outer diameter of the catheter was small enough to allow penetration into the hole, while the inner diameter was large enough to allow passage of the compressed foam into the subcutaneous area of the rat or the mouse. FIGS. 7A-7B shows the exemplary stages of injecting a silk fibroin foam in an animal study. The Foam Ramrod is inserted into the syringe (FIG. 7A). The needle placed within the catheter is used to facilitate the insertion of the catheter in the desired position (FIG. 7B, step 1). After placing the catheter in the desired position within a tissue, the needle can be removed from the needle/catheter. The silk fibroin foam is positioned in the barrel of the catheter using tweezers (FIG. 7B, step 2). The catheter loaded with the silk fibroin foam is then connected to the Catheter Adapter of the injection gun (FIG. 7B, step 3). The Injection Handle of the injection gun is then repeatedly squeezed to slowly inject the foam into the animal (FIG. 7B, step 4).

Figure 8A:
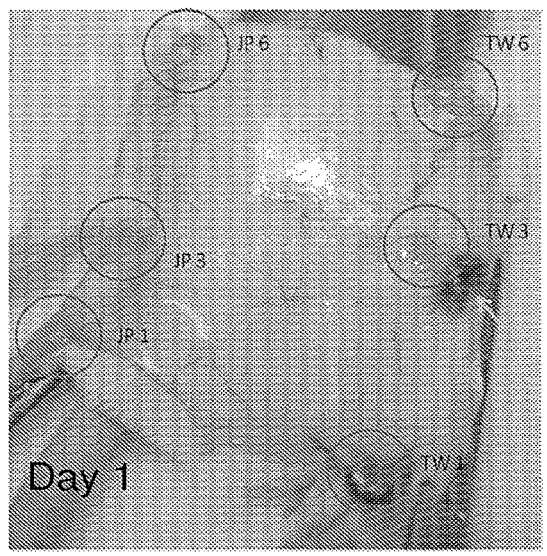
FIGS. 8A-8G show images and results of some embodiments of the silk fibroin-based foams injected into a rat model in vivo.
Figure 8B:
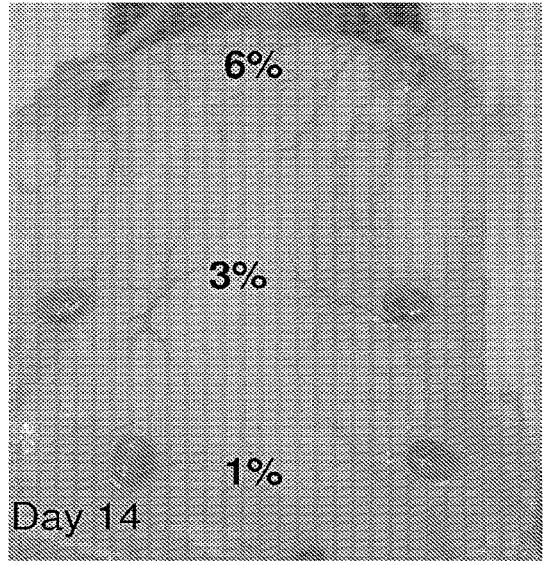
Figure 8C:
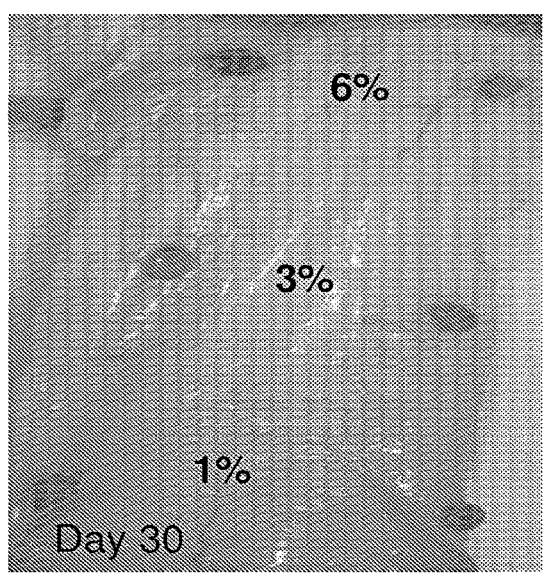
Figure 8D:
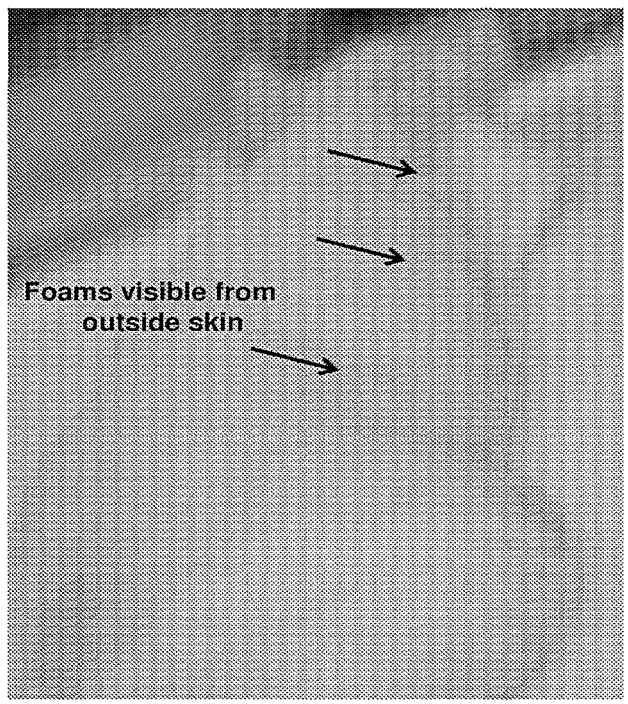
Figure 8E:
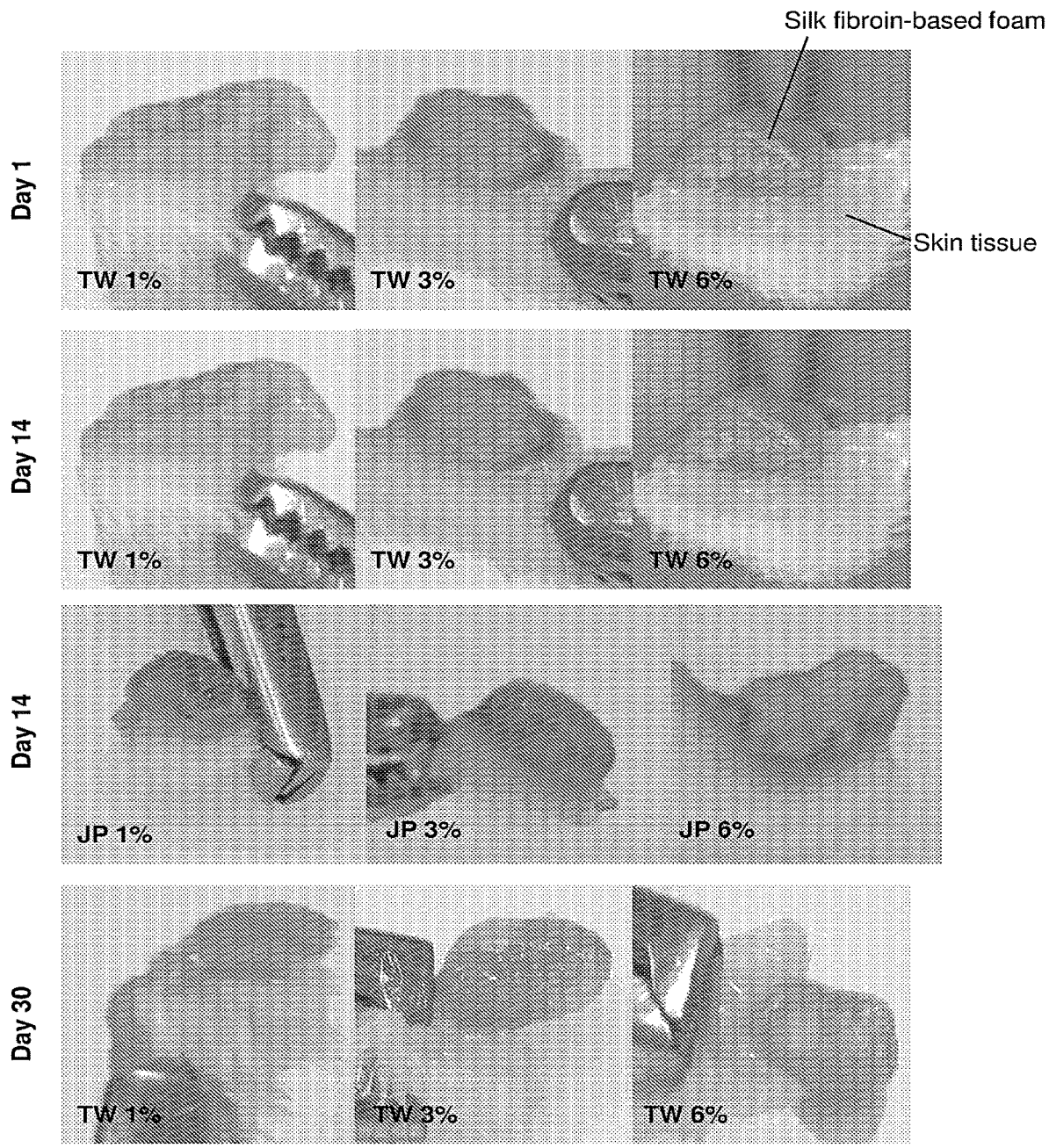

FIGS. 8A-8C show images of silk fibroin-based foams injected into a rat model in vivo after the removal of the rat skin. Silk fibroin-based foams produced from different concentrations of silk fibroin solution (e.g., 1%, 3%, 6% silk fibroin) and sources of cocoon Japanese: JP vs. Taiwanese: TW) were evaluated after injection for 1 day (FIG. 8A), 14 days (FIG. 8B) and 30 days (FIG. 8C). FIG. 8A shows that the injected silk fibroin-based foams remained clear 1 day after injection, unless they were stained by blood due to a puncture into a blood vessel (e.g., TW3). FIGS. 8B-8C show that the injected silk fibroin-based foams obtained a reddish hue about 14 days and about 30 days, respectively, after injection. However, there appeared no significant change in vascularization leading to the injected foams. FIG. 8D shows an image of the injected foams visible from outside skin of a rat. FIG. 8E is a set of images showing gross morphology of the silk fibroin-based injectable foams (corresponding to the ones in FIGS. 8A-8C) explanted after an indicated post-injection period (e.g., 1 day, 14 days and 30 days post-injection). There are no observable visual differences in gross morphology at the indicated timepoints. The silk fibroin foams are consistently stiffer with increased silk weight percentage. All explants are soft to the touch and return to their original shape after deformation. Histology for the explanted silk fibroin foams attached to the tissue is performed to evaluate vascularity and integration with tissues.

Figure 8F:
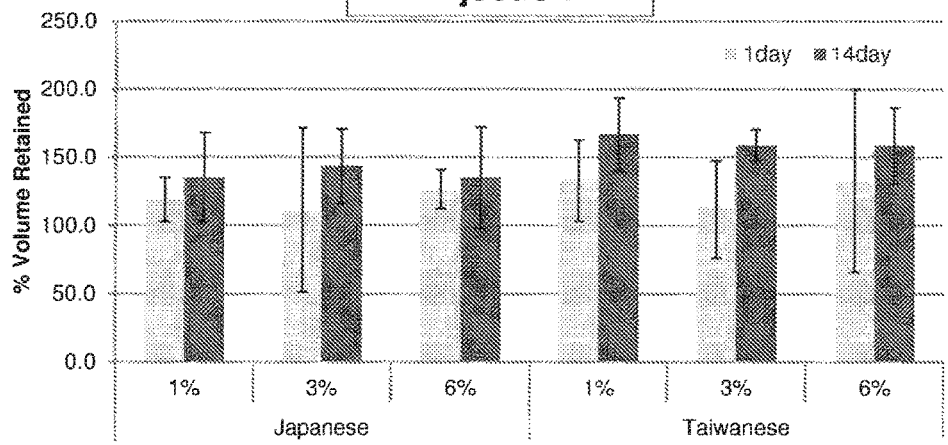
Figure 8G:
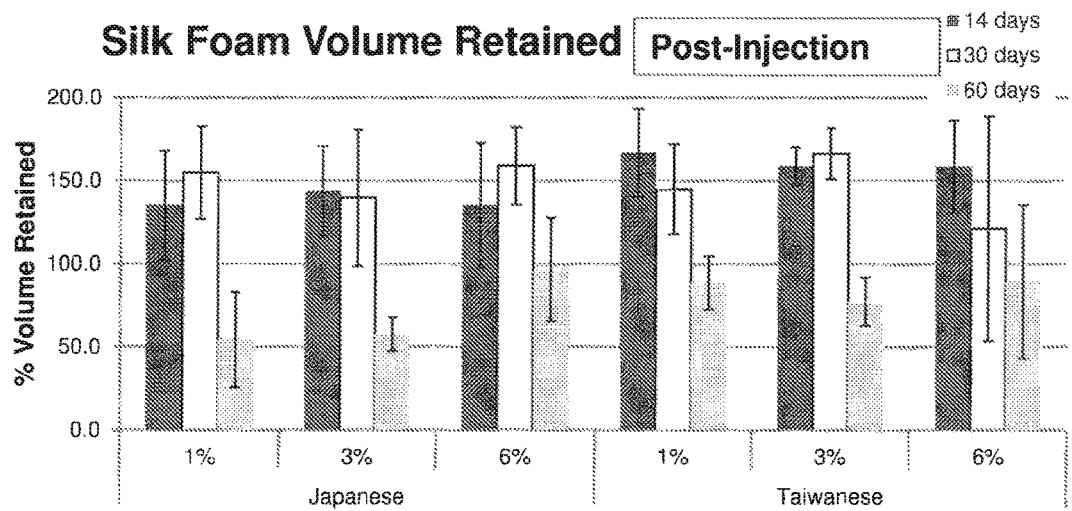

FIG. 8F shows the volume retention results of the silk fibroin-based foams after injection into the rat tissue for 1 day or 14 days. FIG. 8G shows the volume retention results of the silk fibroin-based foams after injection into the tissue for 14 days, 30 days or 60 days. The results of FIGS. 8F and 8G are expressed in percents of volume retained relative to the original volume (i.e., the volume of the silk fibroin-based foams before compression). FIGS. 8F and 8G show that the silk fibroin foams produced from a silk fibroin solution of about 1%, 3%, or 6% can maintain at least about 80% of their original volume (including at least about 90%, at least about 95%, at least about 100% or higher, of their original volume) for at least about 30 days or longer, and at least about 50% or higher of their original volume for at least about 60 days or longer. As shown in FIGS. 8F-8G, the volume retained in the tissue can be greater than the original volume, likely because the silk fibroin-based foams can absorb water and thus swell. The stiffness of the silk fibroin foams generally increases with the concentration of the silk fibroin solution. Thus, silk fibroin foams of higher silk fibroin concentrations can generally maintain their volume for a longer period of time than those of lower silk fibroin concentrations. Further, the silk fibroin foams produced from a silk fibroin solution of about 1%, 3% or 6% remain soft and spongy for at least 60 days after injection into the rat.

Presented herein are some embodiments of the silk fibroin-based foams that can be ejected from a needle, pipette tip, catheter or other tubular structures (e.g., including tubular structures with a tapered end). The silk fibroin-based foams can be compressed prior to injection and then expand, for example, by at least about 2.5-fold, upon released from the compression and/or upon injection into a tissue. In some embodiments, the injected silk fibroin-based foam can have sufficient physical and mechanical integrity to bulge the surface of raw chicken meat and provide a noticeable bulk when injected subcutaneously in a rat (FIG. 8D). The properties of the silk fibroin-based foam can be controlled by various factors, including, but not limited to, degumming time during silk fibroin solution preparation, the concentration of silk fibroin solution used, and the use of a methanol or other suitable treatment to control crystalline (beta sheet) content.

In some embodiments, longer silk fibroin-based foam constructs can be used to fill relatively large soft tissue void spaces through an incision, cannula, needle, pipette tip, catheter, or other tubular structures (e.g., including tubular structures with a tapered end), thus requiring a relatively small hole to be used for tissue penetration, as compared to conventional invasive procedures.

What is claimed is:

1. A method for augmenting a soft tissue in a subject, comprising injecting into the soft tissue to be augmented a composition from an injection applicator, the composition comprising
   (i) a silk fibroin foam;
   (ii) at least one additional material selected from the group consisting of collagen, gelatin, elastin, glycosaminoglycans, hyaluronic acid, and poly(lactic acid),
   wherein the silk fibroin foam has a porosity of at least 50% with pores having a size of about 1 µm to about 1500 µm, the pores forming interconnected void spaces throughout a total volume and surface of the silk fibroin foam,
   wherein the silk fibroin foam is in a compressed state prior to injection and expands from the compressed state upon injection into the soft tissue, and
   wherein the silk fibroin foam does not comprise a hydrogel material; and
   (iii) a carrier in fluid communication with the interconnected void spaces of the silk fibroin foam, and
   wherein the silk fibroin foam and the injection applicator are dimensioned relative to one another to provide compression of the silk fibroin foam when located within the injection applicator prior to injection.

2. The method of claim 1, wherein the silk fibroin foam expands in volume from the compressed state by at least 2-fold relative to the volume of the compressed state.

3. The method of claim 1, wherein the silk fibroin foam, upon injection into the soft tissue, retains at least about 50% of its original expanded volume within the soft tissue for at least about 2 weeks, at least about 6 weeks, at least about 3 months, or at least about 6 months.

4. The method of claim 1, wherein the soft tissue is a breast tissue or a facial tissue.

5. The method of claim 1, wherein the soft tissue is a vocal cord or a glottis.

6. The method of claim 1, wherein the silk fibroin foam comprises glycerol.

7. The method of claim 1, comprising injecting the composition through a 26 g-30 g needle.

8. The method of claim 1, comprising injecting the composition through a 21 g-27 g needle.

9. The method of claim 1, wherein the silk fibroin foam has a porosity of at least 90%.

10. The method of claim 1, wherein the pores have a size of about 25 µm to about 800 µm.

11. The method of claim 1, wherein the silk fibroin foam is formed from a silk fibroin solution of about 0.1% w/v to about 30% w/v.

12. The method of claim 1, wherein the composition further comprises at least one active agent.

13. The method of claim 1, wherein the at least one additional material is hyaluronic acid.

14. The method of claim 1, wherein the silk fibroin foam comprises an anesthetic.

15. The method of claim 1, wherein the carrier comprises a silk fibroin gel phase.

16. An injection applicator comprising an injectable composition for use in augmenting a soft tissue in a subject, the injectable composition comprising
   (i) a silk fibroin foam and
   (ii) at least one additional material selected from the group consisting of collagen, gelatin, elastin, glycosaminoglycans, hyaluronic acid, and poly(lactic acid),
   wherein the silk fibroin foam has a porosity of at least 50% with pores having a size of about 1 µm to about 1500 µm, the pores forming interconnected void spaces throughout a total volume and surface of the silk fibroin foam,
   wherein the silk fibroin foam is in a compressed state prior to injection and expands from the compressed state upon injection into the soft tissue, and
   wherein the silk fibroin foam does not comprise a hydrogel material, and
   (iii) a carrier in fluid communication with the interconnected void spaces of the silk fibroin foam, and wherein the silk fibroin foam and the injection applicator are dimensioned relative to one another to provide compression of the silk fibroin foam when located within the injection applicator prior to injection.

17. The injectable applicator of claim 16, wherein the silk fibroin foam expands in volume from the compressed state by at least 2-fold relative to the volume of the compressed state.

18. The injectable applicator of claim 16, wherein the silk fibroin foam, upon injection into the tissue, retains at least about 50% of its original expanded volume within the soft tissue for at least about 2 weeks, at least about 6 weeks, at least about 3 months, or at least about 6 months.

19. The injectable applicator of claim 16, wherein the pores have a size of about 25 μm to about 800 μm.

20. The injectable applicator of claim 16, wherein the silk fibroin foam is formed from a silk fibroin solution of about 0.1% w/v to about 30% w/v.

21. The injectable applicator of claim 16, wherein the injectable composition further comprises at least one active agent.

22. The injectable applicator of claim 16, wherein the silk fibroin foam, when in the compressed state, has a volume of about 10% to about 90% of its original volume before compression.

23. The injectable applicator of claim 16, wherein the at least one additional material is hyaluronic acid.

24. The injectable applicator of claim 16, wherein the silk fibroin foam comprises an anesthetic.

25. The injectable applicator of claim 16, wherein the carrier comprises a silk fibroin gel phase.

* * * * *

UNITED STATES PATENT AND TRADEMARK OFFICE
CERTIFICATE OF CORRECTION

Page 1 of 2

PATENT NO. : 11,701,450 B2
APPLICATION NO. : 15/273327
DATED : July 18, 2023
INVENTOR(S) : Leisk et al.

It is certified that error appears in the above-identified patent and that said Letters Patent is hereby corrected as shown below:

In the Specification

In Column 3, Line 8, after "applicator", insert --(e.g.,--

In Column 5, Line 9, after "the", insert --silk--

In Column 5, Line 13, after "compressed", insert --silk--

In Column 6, Line 6, delete "dose" and insert --close-- therefor

In Column 7, Line 11, before "fibroin-based", insert --silk--

In Column 7, Line 25, delete "sills" and insert --silk-- therefor

In Column 8, Line 54, after "matrix", insert --(i.e.,--

In Column 17, Line 33, after "the", insert --silk--

In Column 17, Line 49, delete "fibrin" and insert --fibroin-- therefor

In Column 33, Line 15, after "and/or", insert --silk--

In Column 37, Line 21, before "fibroin", insert --silk--

In the Claims

In Column 49, Line 60, in Claim 1, after "comprising", insert --:--

Signed and Sealed this
Tenth Day of September, 2024

Katherine Kelly Vidal
*Director of the United States Patent and Trademark Office*

In Column 50, Line 50, in Claim 16, after "comprising", insert --:--

In Column 50, Line 51, in Claim 16, delete "foam and" and insert --foam;-- therefor